(12) United States Patent
Hisamichi et al.

(10) Patent No.: US 6,432,963 B1
(45) Date of Patent: Aug. 13, 2002

(54) PYRIMIDINE-5-CARBOXAMIDE DERIVATIVES

(75) Inventors: Hiroyuki Hisamichi; Ryo Naito; Souichirou Kawazoe; Akira Toyoshima; Kazuhito Tanabe; Eiichi Nakai; Atsushi Ichikawa; Akiko Orita; Makoto Takeuchi, all of Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/581,595

(22) PCT Filed: Dec. 14, 1998

(86) PCT No.: PCT/JP98/05643
§ 371 (c)(1),
(2), (4) Date: Jun. 15, 2000

(87) PCT Pub. No.: WO99/31073
PCT Pub. Date: Jun. 24, 1999

(30) Foreign Application Priority Data

Dec. 15, 1997 (JP) .............................................. 9-344588

(51) Int. Cl.[7] .................... C07D 239/48; C07D 401/12; A61K 31/505; A61P 37/08
(52) U.S. Cl. ........................ 514/256; 514/269; 514/272; 514/273; 514/275; 544/310; 544/311; 544/316; 544/317; 544/320; 544/321; 544/323; 544/324; 544/328; 544/329; 544/331; 544/332; 544/333; 544/335
(58) Field of Search ................................ 514/256, 269, 514/272, 273, 275; 544/310, 311, 316, 317, 320, 321, 323, 324, 328, 329, 331, 332, 333, 335

(56) References Cited

U.S. PATENT DOCUMENTS

| | | | |
|---|---|---|---|
| 3,901,887 A | 8/1975 | Santilli et al. | 260/256.5 R |
| 5,104,877 A | 4/1992 | Boger | 514/256 |
| 5,216,023 A | 6/1993 | Literati Nagy et al. | 514/538 |
| 5,250,548 A | 10/1993 | Winn et al. | 514/340 |
| 5,935,966 A * | 8/1999 | Suto et al. | 514/275 |

FOREIGN PATENT DOCUMENTS

| | | |
|---|---|---|
| DE | 3338859 A1 * | 5/1989 |
| EP | 0 073 328 A1 | 3/1983 |
| EP | 0 475 206 A2 | 3/1992 |
| JP | 4-261156 | 9/1992 |
| WO | 97/19065 | 5/1997 |

OTHER PUBLICATIONS

Roy. S.K., et al, "Antifungal Activity of 2,4–Disubstituted Pyrimidine–5–carboxylates", Indian J. Chem., vol. 16B, Oct. 1978, pp. 932–933.
International Search Report PCT/JP98/05643 Feb. 16, 1999.

* cited by examiner

Primary Examiner—Richard L. Raymond
Assistant Examiner—Thomas C McKenzie
(74) Attorney, Agent, or Firm—Sughrue Mion, PLLC

(57) ABSTRACT

Pyrimidine-5-carboxamide derivatives represented by a general formula (I) or salts thereof

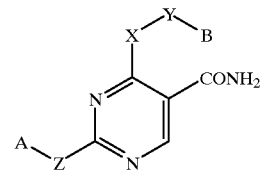

[wherein each symbol has the following meaning;

X: O, S, $NR^1$, CO, $NR^1CO$, $CONR^1$, $C=N-OR^1$ or a bond,

Y: a lower alkylene group which may be substituted by $OR^1$ or $-NHR^1$, or a bond, Z: O, $NR^2$ or a bond, A: H, or a lower alkyl which may have a substituent, a —CO-lower alkyl which may have a substituent, an aryl which may have a substituent, a heteroaryl which may have a substituent, a cycloalkyl which may have a substituent or a nitrogen-containing saturated heterocyclic group which may have a substituent, B: an aryl which may have a substituent or a heteroaryl group which may have a substituent, $R^1$, $R^2$: H, a lower alkyl or a —CO-lower alkyl group].

6 Claims, No Drawings

PYRIMIDINE-5-CARBOXAMIDE DERIVATIVES

TECHNICAL FIELD

This invention relates to medicaments, particularly pyrimidine-5-carboxamide derivatives having Syk tyrosine kinase inhibition activity.

BACKGROUND ART

It is known that type I (immediate type) allergic reaction such as bronchial asthma, allergic rhinitis or atopic dermatitis is mediated mainly by the interaction between immunoglobulin E (IgE) and mast cells or basophiles. Mast cells and basophiles have an Fc receptor (FcεRI) having high affinity for IgE. Firstly, IgE binds to FcεRI and then antigens such as pollen, house dust or the like cross-link the receptor by binding to its specific IgE, thereby making progress of an allergic reaction. As a result of such a response, cytoplasmic secretory granules containing inflammatory mediators such as histamine, leukotriene and the like are released, which cause acute inflammatory reactions, and production of cytokine which takes part in various allergic and inflammatory reactions is accelerated.

It is known that at least two types of protein tyrosine kinase, Lyn (Eiseman, E. and Bolen, J. B., *Nature*, 355: 78–80 (1992)) and Syk (Taniguchi, T. et al., *J. Biol. Chem.*, 266: 15790–15796 (1991)), are concerned in the intracellular signal transduction accompanied by this FcεRI activation. These tyrosine kinases are activated (tyrosine phosphorylated) after crosslinking of FcεRI by antigens (Hutchcroft, J. E. et al., *Proc. Natl. Acad. Sci. USA*, 89: 9107–9111 (1992)). It has been shown also that the SH2 domain and tyrosine kinase activity of Syk are necessary for the degranulation and cytokine production acceleration induced by the activation of FcεRI (Rivera, V. M. and Brugge, J. S., *Mol. Cell. Biol.*, 15: 1582–1590 (1995)).

In consequence, it is expected that the release of mediators and the production of cytokines concerned in IgE stimulation-dependent allergic and inflammatory reactions from mast cells and basophiles can be controlled by inhibiting the tyrosine kinase activity of Syk.

It has been reported that the tyrosine phosphorylation of intracellular protein (activation) induced by stimulation of a receptor for IgG antibody, FcγR, and the phagocytosis mediated by FcγR are considerably inhibited in macrophages derived from Syk deficient mouse (Crowley, M. T. et al., *J. Exp. Med.*, 186: 1027–1039 (1997)), suggesting that Syk has a markedly important role in the FcγR-mediated phagocytosis of macrophage. In consequence, there is a possibility that Syk inhibitors can inhibit cell or tissue damage induced by antibody-dependent cellular cytotoxicity (ADCC).

It has been reported that an antisense oligonucleotide of Syk suppresses the apoptosis inhibition of eosinophils induced by GM-CSF (Yousefi, S. et al., *J. E. Med.*, 183: 1407–1414 (1996)), showing that Syk is essential for the life extending signal of eosinophils caused by GM-CSF and the like. Since life extension of eosinophils is closely related to the transition of diseases into a chronic state in allergic disorders such as asthma, Syk inhibitors can also become therapeutic agents for chronic eosinophilic inflammation.

Syk is important for the activation of B cells via a B cell antigen receptor and deeply concerned in the phosphatidylinositol metabolism and increase in the intracellular calcium concentration caused by the antigen receptor stimulation (Hutchcroft, J. E. et al., *J. Biol. Chem.*, 267: 8613–8619 (1992) and Takata, M. et al., *EMBO J.*, 13: 1341–1349 (1994)). In consequence, Syk inhibitors have a possibility of controlling the function of B cells and therefore are expected as therapeutic agents for antibody-related diseases.

Syk binds to a T cell antigen receptor, quickly undergoes tyrosine phosphorylation through crosslinking of the receptor and synergistically acts upon intracellular signals in which tyrosine kinases essential for the T cell activation such as Lck takes part (Couture, C. et al., *Proc. Natl. Acad. Sci. USA*, 91: 5301–5305 (1994) and Couture, C. et al., *Mol. Cell. Biol.*, 14: 5249–5258 (1994)). In consequence, it is suggested that Syk inhibitors have a potential to be agents for inhibiting cellular immunity mediated by T cell antigen receptor.

Release of arachidonic acid and serotonin and platelet aggregation induced by collagen are markedly-inhibited in platelets derived from Syk deficient mouse (Poole, A. et al., *EMBO J.*, 16: 2333–2341 (1997)), so that an anticoagulation action is also expected in Syk inhibitors.

On the other hand, WO 97/19065 discloses that a 2-anilinopyrimidine derivative represented by the following formula selectively inhibits p56$^{lck}$, p59$^{fyn}$, ZAP-70 and protein kinase C. However, it does not disclose or suggest about its action upon Syk.

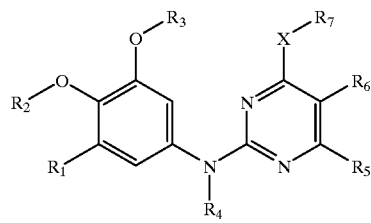

(In the formula, $R_6$ represents H, —$NH_2$, substituted amino, nitro, —COOH, ester or the like. See said document for other symbols.)

As pyrimidine compounds having substituted amino group at the 4-position and carboxamido group at the 5-position, the following compound

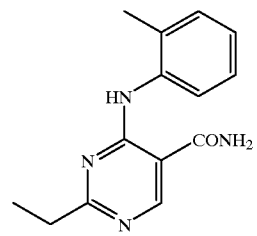

is disclosed in Indian *J. Chem., Sect. B*, 16 (B) (10), 932–933 (1978), and the following compound

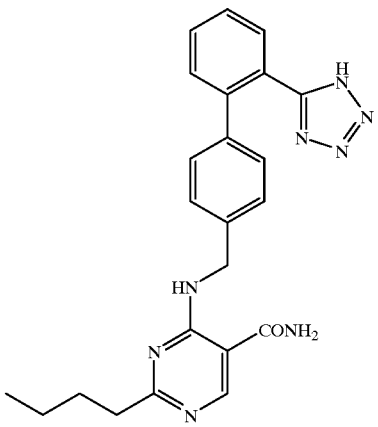

is disclosed in EP 475206 and U.S. Pat. No. 5,104,877. However, there is no disclosure or suggestion about the action of these compounds upon Syk.

Also, antilipidemic activity of pyrimidine compounds having a phenylamino group at the 4-position is disclosed in EP 73328, U.S. Pat. No. 3,901,887, U.S. Pat. No. 3,910,910 and U.S. Pat. No. 3,940,394. However, these compounds do not have a carboxamido group at the 5-position, and there is no disclosure about the action upon Syk.

A plant natural product, Piceatannol, has so far been reported as a Syk tyrosine kinase inhibitor (Oliver, J. M. et al., *J. Biol. Chem.*, 269: 29697–29703 (1994)). However, since its in vitro Syk kinase inhibition activity is weak, great concern has been directed toward the creation of more excellent Syk tyrosine kinase inhibitor.

DISCLOSURE OF THE INVENTION

The present inventors have made extensive studies on compounds capable of inhibiting tyrosine kinase activity of Syk and, as a result, found that a pyrimidine derivative having a carboxamido group at the 5-position has excellent Syk tyrosine kinase inhibitory activity and a:Th is useful as an agent for preventing, treating or diagnosing diseases in which Syk takes part, and thereby have accomplished the invention.

Accordingly, the present invention relates to a pyrimidine-5-carboxamide derivative represented by the following general formula (I) or a salt thereof.

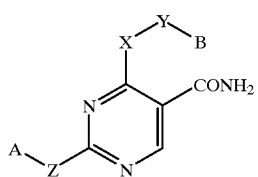

(I)

[In the formula, each symbol has the following meaning;
X: O, S, NR$^1$, CO, NR$^1$CO, CONR$^1$, C=N—OR$^1$ or a bond,
Y: a lower alkylene group which may be substituted by OR$^1$ or —NHR$^1$, or a bond,
Z: O, NR$^2$ or a bond,
A: H, or a lower alkyl which may have a substituent, a —CO-lower alkyl which may have a substituent, an aryl which may have a substituent, a heteroaryl which may have a substituent, a cycloalkyl which may have a substituent or a nitrogen-containing saturated heterocyclic group which may have a substituent,
B: an aryl which may have a substituent (provided that 2'-(1H-tetrazol-5-yl)biphenyl-4-yl group is excluded) or a heteroaryl group which may have a substituent, and
R$^1$, R$^2$: H, a lower alkyl or a —CO-lower alkyl group. The same shall apply hereinafter.]

Also, according to the present invention, there is provided a pharmaceutical composition, particularly a Syk tyrosine kinase inhibitor, which comprises the aforementioned pyrimidine-5-carboxamide derivative or a salt thereof.

The following further describes the compound of general formula (I).

In this specification, the term "lower" means a straight or branched hydrocarbon chain having from 1 to 6 carbon atoms. The "lower alkyl group" is preferably a lower alkyl group having from 1 to 4 carbon atoms, more preferably a methyl group, an ethyl group or an isopropyl group. The "lower alkylene group" is preferably a methylene group.

The "aryl group" is preferably a monocyclic to tricyclic aryl group having from 6 to 14 carbon atoms, more preferably, a phenyl group or a naphthyl group. Also, the phenyl group may be condensed with a five- to eight-membered cycloalkyl ring to form, for example, an indanyl group or a 5,6,7,8-tetrahydronaphthyl group, which is connected to the aromatic ring. The "cycloalkyl group" is preferably a cycloalkyl group having from 3 to 8 carbon atoms, more preferably a cyclopropyl group, a cyclopentyl group or a cyclohexyl group. Also, the cycloalkyl group may be condensed with a benzene ring to form, for example, 1- or 2-indanyl or a 1,2,3,4-tetrahydronaphthyl group.

The "nitrogen-containing saturated heterocyclic group" is a five- to eight-membered saturated heterocyclic group which has at least one N as a ring atom and may further have one O or S, and is preferably pyrrolidinyl, piperidyl, morpholinyl, piperazinyl, pyrazolidinyl, imidazolidinyl or homopiperazinyl. The "saturated heterocyclic group" is a five- to eight-membered saturated heterocyclic group having from 1 to 4 hetero atoms selected from O, S and N, and it preferably includes tetrahydrofuranyl and tetrahydropyranyl, in addition to the groups described in the aforementioned "nitrogen-containing saturated heterocyclic group".

The "heteroaryl group," is a five- to eight-membered monocyclic heteroaryl group having from 1 to 4 hetero atoms selected from 0, S and N, and it preferably includes pyridyl, pyrimidinyl, imidazolyl, thienyl, furyl and thiazolyl groups.

Substituents of the "lower alkyl which may have a substituent", "aryl which may have a substituent", "heteroaryl which may have a substituent", "cycloalkyl which may have a substituent" and "nitrogen-containing saturated heterocyclic group which may have a substituent" are not particularly limited so long as they can be used as substituents of these rings; but are preferably the substituents described in the following.

Substituents in the "cycloalkyl which may have a substituent" and "nitrogen-containing saturated heterocyclic group which may have a substituent" are preferably the groups selected from the following Group a, and they may have from 1 to 4 of these substituents. Particularly preferred are —NH$_2$, —NH$_2$ in a prodrug form and -lower alkylene-NH$_2$.

Group a: —NH$_2$, —NH$_2$ in a prodrug form, -lower alkylene-NH$_2$, -lower alkylene-NH$_2$ in a prodrug form, —NH-lower alkyl, —N(lower alkyl)$_2$, —NH-lower alkylene-aryl, —NH-aryl, —NH-cycloalkyl, —NH-heteroaryl, —NHCO-lower alkyl, —NHSO$_2$-lower alkyl, —NHC(NH)NH$_2$, —NHCONH$_2$, —OH, —O-lower alkyl, —CO$_2$H, —CONHOH, —CO$_2$-lower alkyl, —CONH-lower alkyl and —CON(lower alkyl)$_2$.

Substituents of the "aryl which may have a substituent", "heteroaryl which may have a substituent" are preferably the groups selected from the aforementioned Group a and the following Group b, and they may have from 1 to 4 of these substituents. Particularly preferred are —NH$_2$, -lower alkylene-NH$_2$, -lower alkyl, -halogen atom (F, Cl, Br or I), —CF$_3$ and —O-lower alkyl group.

Group b: -lower alkyl, -halogen atom (F, Cl, Br or I), -lower alkyl substituted by a halogen atom (—CH$_2$F, —CHF$_2$, —CF$_3$ or the like), —O-lower alkylene-aryl, —O-aryl, —O-lower alkylene-aryl-O-lower alkyl, —S-lower alkylene-aryl, —S-lower alkylene-aryl-O-lower alkyl, —NO$_2$ and —CN.

The substituent of the "lower alkyl group which may have a substituent" is preferably a group selected from the aforementioned Group a and the following Group c, and it may have from 1 to 4 of these substituents. Particularly preferred are —NH$_2$ and —NH$_2$ in a prodrug form.

Group c: -halogen atom (F, Cl, Br or I), —O-lower alkylene-aryl, —O-aryl, —O-lower alkylene-aryl-O-lower alkyl, —S-lower alkylene-aryl, —S-lower alkylene-aryl-O-lower alkyl, —NO$_2$, —CN, -aryl which may be substituted by a group selected from the Group a, -cycloalkyl, -heteroaryl, -saturated hetero ring, -vinyl, -(1-propenyl) and -ethynyl.

Also, the "—NH$_2$ in a prodrug form" means the groups well known by those skilled in the art, which becomes —NH$_2$ under physiological conditions. Preferred are (Z)-3-[2-(acetoxy)phenyl]-2-propenoylamino-, (acetoxy)methoxycarbonylamino-, 4-azidobenzyloxycarbonylamino-, (5-methyl-2-oxo-1,3-dioxol-4-en-4-yl)methoxycarbonylamino- and [(2-hydroxyphenyl)(phenyl)methylidene]amino-, and other groups of this type known by those skilled in the art are also included.

In addition, the term "bond" means that the corresponding group does not exist, and the groups of both sides are directly linked.

Among compounds of the present invention, the following compounds can be cited as most preferred compounds: 2-(2-aminoethylamino)-4-(3-methylanilino)pyrimidine-5-carboxamide, 2-(2-aminoethylamino)-4-(3-trifluoromethylanilino)pyrimidine-5-carboxamide, 2-(4-aminobutylamino)-4-(3-trifluoromethylanilino)pyrimidine-5-carboxamide, 2-(2-aminoethylamino)-4-(3-bromoanilino)pyrimidine-5-carboxamide, 2-(2-aminoethylamino)-4-(3-nitroanilino)pyrimidine-5-carboxamide, 2-(2-aminoethylamino)-4-(3,5-dimethylanilino)pyrimidine-5-carboxamide, 2-(2-aminoethylamino)-4-(2-naphthylamino)pyrimidine-5-carboxamide, 2-(cis-2-aminocyclohexylamino)-4-(3-methylanilino)pyrimidine-5-carboxamide, 2-(cis-2-aminocyclohexylamino)-4-(3-bromoanilino)pyrimidine-5-carboxamide, 2-(cis-2-aminocyclohexylamino)-4-(3,5-dichloroanilino)pyrimidine-5-carboxamide and 2-(cis-2-aminocyclohexylamino)-4-(3,4,5-trimethoxyanilino)pyrimidine-5-carboxamide.

Depending on the kinds of substituents, the compound of the present invention may exist in the form of geometrical isomers or tautomers, and isolated forms or mixtures of these isomers are included in the present invention. Also, the compound of the present invention may contain an asymmetric carbon atom in some cases, so that isomers based on the asymmetric carbon atom can exist. Mixtures or isolated forms of these optical isomers are included in the present invention.

Also, the compound of the present invention sometimes forms an acid addition salt or, depending on the kinds of substituent groups, a salt with a base. Such salts are pharmaceutically acceptable salts, and their illustrative examples include acid addition salts with inorganic acids (e.g., hydrochloric acid, hydrobromic acid, hydroiodic acid, sulfuric acid, nitric acid, phosphoric acid and the like) or with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), salts with inorganic bases (e.g., sodium, potassium, magnesium, calcium, aluminum and the like) or with organic bases (e.g., methylamine, ethylamine, ethanolamine, lysine, ornithine and the like), ammonium salts, and the like. In addition, various types of hydrates and solvates and polymorphic substances of the compound (I) of the present invention and salts thereof are also included in the present invention.

Production Methods

The compound of the present invention and pharmaceutically acceptable salt thereof can be produced by applying various known synthesis methods, making use of L: their characteristics based on the basic structures or kinds of substituents. In this regard, depending on the kinds of functional groups, it is sometimes effective in view of the production techniques to replace said functional group by an appropriate protecting group, namely a group which can be easily converted into said functional group, at the step of the starting material or intermediate. Thereafter, the desired compound can be obtained by removing the protecting group as occasion demands. Examples of such functional groups include an amino group, a hydroxyl group, a carboxyl group and the like and examples of their protecting groups include the protecting groups described in "Protective Groups in Organic Synthesis (2nd. Ed.)" edited by Greene and Wuts, and these groups are optionally used depending on the reaction conditions.

The following describes typical production methods of the compound of the present invention.

Production method A

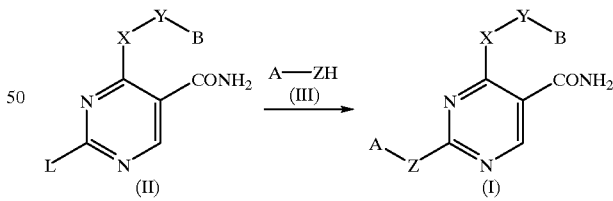

(In the formulae, L represents a leaving group. The same shall apply hereinafter.)

This production method is a method in which the s:compound of the present invention represented by the general formula (I) is obtained by allowing a compound (II) to react with a compound (III). In this regard, examples of the leaving group L include halogen atoms and methylsulfanyl, 1H-benzotriazol-1-yloxy, methanesulfonyloxy, p-toluenesulfonyloxy, trifluoromethanesulfonyloxy and the like.

The reaction can be carried out from at room temperature to under heat reflux using the compounds (II) and (III) in equimolar amounts, or one of them in an excess amount, without solvent or in a solvent inert to the reaction such as aromatic hydrocarbons (e.g., benzene, toluene, xylene and the like), ethers (e.g., diethyl ether, tetrahydrofuran (THF), dioxane and the like), halogenated hydrocarbons (e.g., dichloromethane, 1,2-dichloroethane, chloroform and the like), and N,N-dimethylformamide (DMF), dimethyl acetamide (DMA), N-methylpyrrolidone, ethyl acetate, acetonitrile and the like. The reaction temperature can be optionally selected depending on the compounds. Depending on the compounds, it is advantageous in some cases to carry out the reaction in the presence of an organic base (preferably diisopropylethylamine, N-methylmorpholine, pyridine or 4-(N,N-dimethylamino)pyridine) or a metal salt base (preferably potassium carbonate or sodium hydroxide).

Production method B

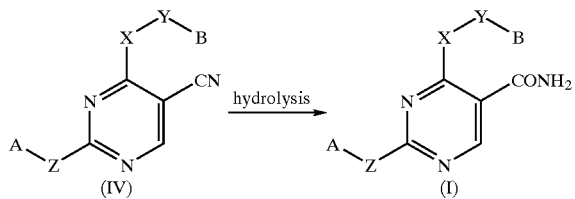

(Symbols in the formulae are as defined in the foregoing.)

This production method is a method in which the compound (I) of the present invention is obtained by converting the nitrile group of a nitrile compound (IV) into a carboxamido group under various conditions. The reaction can be carried out from at room temperature to under heat reflux without solvent or in an reaction inert solvent such as aromatic hydrocarbons, ethers, halogenated hydrocarbons, alcohols (e.g., methanol, ethanol and the like), DMF, pyridine, water, dimethyl sulfoxide (DMSO) and the like, in the presence of a mineral acid (e.g., sulfuric acid, hydrochloric acid, hydrobromic acid or the like), an organic acid (e.g., formic acid, acetic acid or the like), or a base (e.g., sodium hydroxide, potassium hydroxide, potassium carbonate, sodium carbonate, ammonia or the like). It is advantageous in some cases to carry out the reaction in the presence of hydrogen peroxide or the like, in effecting smooth progress of the reaction. The reaction temperature can be selected optionally, depending on the compound.

Production method C

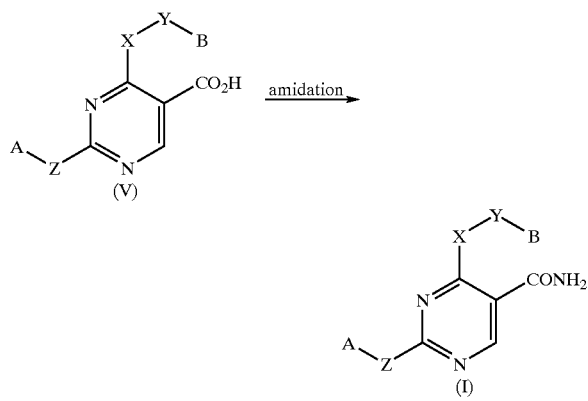

(Symbols in the formulae are as defined in the foregoing.)

This production method is a method in which the compound (I) of the present invention is obtained by converting the carboxyl group of a compound (V) into carboxamido group under various conditions.

The production reaction can be carried out by treating the carboxylic acid compound (V) with ammonia without solvent or in a solvent inert to the reaction such as aromatic hydrocarbons, ethers, halogenated hydrocarbons, DMF, DMA, N-methylpyrrolidone, pyridine, DMSO, ethyl acetate, acetonitrile and the like, in the presence of a condensing agent (e.g., dicyclohexylcarbodiimide (DCC), diisopropylcarbodiimide (DIPC), 1-ethyl-3-(3-dimethylaminopropyl)carbodiimide (WSC), 1,1'-carbonylbis-1H-imidazole (CDI) or the like) and, in some cases, an additive agent such as N-hydroxysuccinimide (HONSu), 1-hydroxybenzotriazole (HOBt) or the like. The reaction can be carried out from under cooling to under heat reflux and the reaction temperature can be selected optionally depending on the compound.

In this regard, when the compound (I) of the present invention in this production method has a hydroxyl group, an amino group and the like, these functional groups of the carboxylic acid compound (V) are protected in advance with a protecting group, and the protecting group is removed after completion of the reaction of the production method C. As the protecting group, it may be selected optionally from the protecting groups described in the aforementioned "Protective Groups in Organic Synthesis (2nd. Ed.)".

Production method D

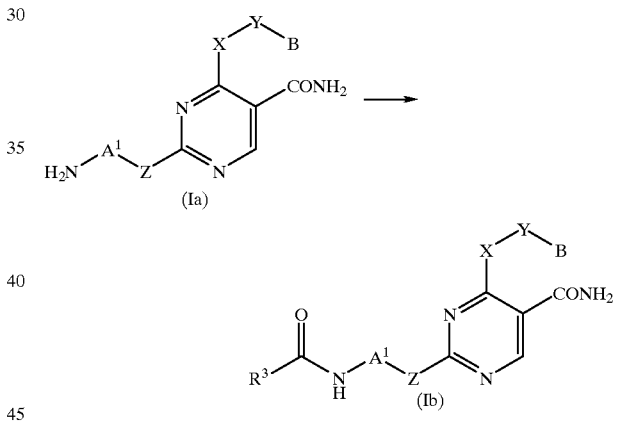

(In the above formulae, $R^3$ means a lower alkyl or $R^3$—CONH— as an amino group in a prodrug form, $A^1$ taken together with $NH_2$ or $R^3$—CONH— or a group derived from $NH_2$ which will be described later represents A, and other symbols are as defined in the foregoing.)

This production method is a method in which a compound (Ib) of the present invention is obtained by allowing the amino group of a compound (Ia) having an amino group on A to react with a carboxylic acid compound.

In this reaction, condensation is effected for example by an acid halide method, a mixed or a symmetric acid anhydride method, an active ester method or a condensing agent (DCC, WSC, CDI or the like) method in an inert solvent such as halogenated hydrocarbons, ethers, DMF or the like from under cooling to under heating, preferably at from −20° C. to 60° C. It is advantageous in some cases to carry out the reaction in the presence of an organic base, from the viewpoint of effecting smooth progress of the reaction.

Production method E

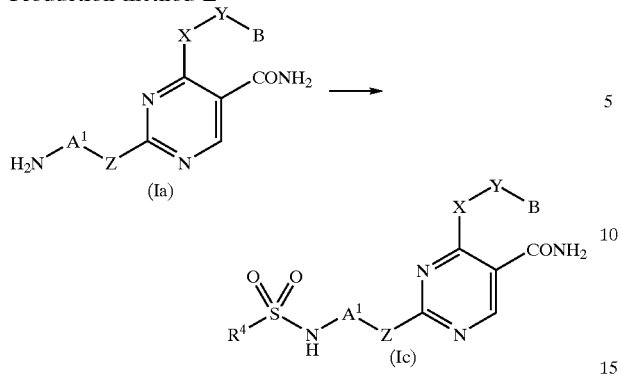

(In the formulae, $R^4$ represents a lower alkyl, and other symbols are as defined in the foregoing.)

This production method is a method in which a compound (Ic) is obtained by carrying out sulfonylation of the amino group of the compound (Ia) having an amino group on A.

In this reaction, condensation of a sulfonyl chloride compound with the compound (Ia) is carried out in an inert solvent such as halogenated hydrocarbons, ethers, DMF or the like from under cooling to under heating, preferably at from −20° C. to 60° C. It is advantageous in some cases to carry out the reaction in the presence of an organic base, from the viewpoint of effecting smooth progress of the reaction.

Production method F

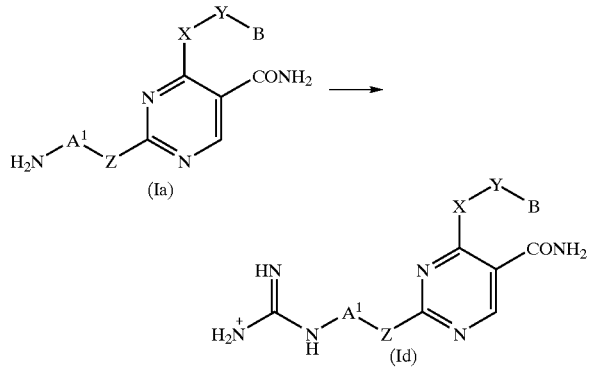

(Symbols in the formulae are as defined in the foregoing.)

This production method is a method in which a compound (Id) of the present invention having a guanidino group is produced from the compound (Ia) having an amino group on A.

The reaction is carried out using the amine compound and an guanidino adding agent such as 3,5-dimethylpyrazole-1-carboxamidine nitrate, cyanamide, isothiourea derivatives, isourea derivatives or the like without solvent or in a solvent inert to the reaction such as aromatic hydrocarbons, ethers, halogenated hydrocarbons, alcohols, water, DMF, DMA, N-methylpyrrolidone, pyridine, DMSO, ethyl acetate, acetonitrile and the like. It is advantageous in some cases to carry out the reaction in the presence of an organic base or a metal salt base, from the viewpoint of effecting smooth progress of the reaction. These solvents may be used alone or as a mixture of two or more. The reaction can be carried out from under cooling to under heat reflux. The reaction temperature can be selected optionally depending on the compounds.

Production method G

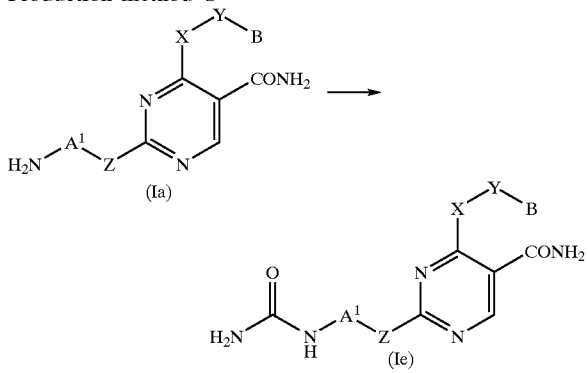

(Symbols in the formulae are as defined in the foregoing.)

This production method is a method in which a compound (Ie) having a urea group is produced from the compound (Ia) having an amino group on A.

This reaction is carried out using the amine compound, a urea adding agent such as a cyanic acid derivative (e.g., sodium cyanate, potassium cyanate or the like), isocyanate derivative, urea, cyanogen bromide or the like, without solvent or in a solvent inert to the reaction such as aromatic hydrocarbons, ethers, halogenated hydrocarbons, alcohols, water, DMF, DMA, N-methylpyrrolidone, pyridine, DMSO, ethyl acetate, acetonitrile and the like. It is advantageous in some cases to carry out the reaction in the presence of an acid such as acetic acid, hydrochloric acid or the like or an base such as sodium hydroxide, potassium hydroxide, from the viewpoint of effecting smooth progress of the reaction. These solvents may be used alone or as a mixture of two or more. The reaction can be carried out from under cooling to under heat reflux. The reaction temperature can be selected optionally depending on the compounds.

Production method H

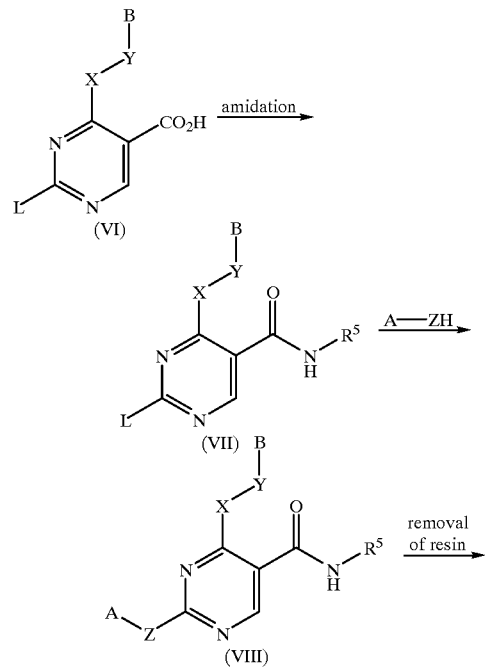

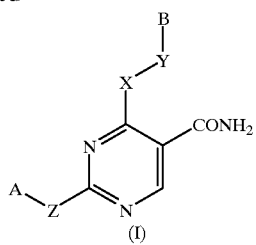

(In the formulae, $R^5$ represents a resin for solid phase synthesis, and other symbols are as described in the foregoing.)

This production method is a solid phase synthesis method which comprises the following three steps.

(1) Fix to a Resin By Amidation

A compound (VII) can be obtained by effecting condensation of a carboxylic acid compound (VI) with an amino terminal-containing resin for solid phase synthesis (e.g., amino(methyl) resin, Rink amide resin or the like) in the same manner as the case of production method C.

(2) Introduction of Substituent Group

A compound (VIII) can be produced in the same manner as described in the production method A.

(3) Removal of Resin

The compound (I) of the present invention is produced by eliminating the resin from the compound (VIII). The reaction is carried out by treating it with a mineral acid or organic acid without solvent or in a solvent inert to the reaction such as aromatic hydrocarbons, ethers, halogenated hydrocarbons, alcohols, DMF, DMA, N-methylpyrrolidone, pyridine, DMSO, ethyl acetate, acetonitrile and the like. It is advantageous in some cases to carry out the reaction in the presence of an additive agent such as difluoroethanol, triethylsilane, triisopropylsilane, (thio)anisole or the like.

Production Method of Starting Compounds

Starting compounds for the compound of the present invention can be produced in the usual way, for example, by applying known reactions shown in the following synthetic pathway diagram.

Production method 1

The substitution reaction can be carried out in the same manner as the case of the aforementioned production method A. It is desirable to carry out the reaction in a solvent such as acetonitrile or the like in the presence of an organic base when X is $NR^2$, or in a solvent such as DMF or the like in the presence of a metal salt base when X is O or S. Regarding the hydrolysis, when $R^6$ is nitrile group, the amide compound (II) can be obtained by carrying out the same procedure of the aforementioned production method B and, when $R^6$ is an ester group, the carboxylic acid compound (VI) can be obtained by treating with an acid or alkali in the usual way. The amidation can be carried out in the same manner as the case of the aforementioned production method C. In carrying out the amidation, the leaving group L may be substituted by other group (benzotriazol-1-yloxy, imidazolyl, amino or the like) depending on the conditions.

Production method 2

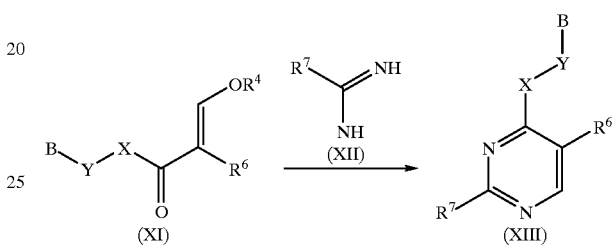

(In the formulae, $R^7$ represents a lower alkyl or methylsulfanyl group, and other symbols are as defined in the foregoing.)

This production method is a method in which a pyrimidine ring is formed by allowing an alkoxymethylene compound (XI) to react with an amidine or isothiourea compound (XII) under a neutral or basic condition. Water, methanol, ethanol, 1,4-dioxane, pyridine or the like can be used as the solvent. These solvents may be used alone or as a mixture of two or more. Examples of the base to be used include potassium carbonate, sodium carbonate, sodium bicarbonate, sodium hydroxide, potassium hydroxide, sodium ethoxide and the like. The reaction can be carried out

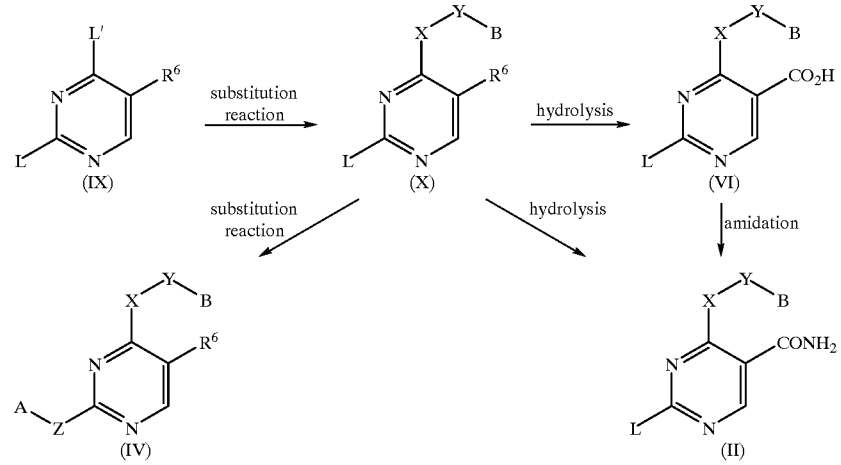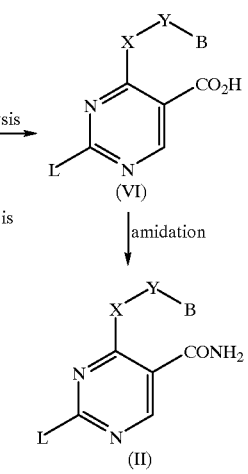

(In the formulae, $R^6$ represents an ester or nitrile group and L' represents a leaving group. The same shall apply hereinafter.)

generally from under room temperature to under heat reflux. The reaction temperature can be optionally selected depending on the compounds.

The reaction product obtained by each of the aforementioned production methods is isolated and purified as a free compound, a salt thereof or various types of solvate such as hydrate. Salts can be produced by usual salt formation treatment.

The isolation and purification are carried out by employing usual chemical operations such as extraction, concentration, evaporation, crystallization, filtration, recrystallization, various chromatographic techniques and the like.

Various isomers can be isolated in the usual way making use of a physicochemibal difference among isomers. For example, optical isomers can be separated by a general optical resolution method such as fractional crystallization or a chromatography. I n addition, an optical isomer can also be produced from an appropriate optically active material compound.

Industrial Applicability

The compound of the invention is useful as an active ingredient for pharmaceutical preparations. Particularly, since it has the action to inhibit Syk tyrosine kinase activity, it is useful as agents for preventing and treating diseases in which Syk takes part, including those diseases in which an allergic or inflammatory reaction becomes the main cause, such as allergic diseases (e.g., asthma, rhinitis, atopic dermatitis, contact dermatitis, nettle rash, food allergy, conjunctivitis, vernal conjunctivitis and the like), autoimmune diseases (e.g., rheumatoid arthritis, systemic lupus erythematosus, psoriasis and the like, ulcerative diseases (e.g., ulcerative colitis and the like), fibrosing diseases, osteoarthritis, cancers and the like; diseases in which immune reaction takes part, such as rejection at the time of organ transplantation and graft versus host disease and the like; diseases in which ADCC takes part, such as autoimmune hemolytic anemia, myasthenia gravis and the like; and diseases in which platelet agglutination takes part, such as thrombosis and the like.

Actions of the compound of the invention have been confirmed by the following pharmacological tests.

1. Syk Tyrosine Kinase Inhibition Test

1) Preparation of Syk Protein:

Human Syk gene, in which a gene of FLAG tag consisting of 8 amino acid residues was linked to the 3'-end, was cloned using RT-PCR method from total RNA prepared from Jurkat cells. The amplified cDNA was incorporated into a vector, pFASTBAC HT, contained in Baculovirus Expression System (GIBCO BRL Inc.). The pFASTBAC HT is designed in such a manner that a His tag consisting of 6 histidine residues can be fused to the 5'-end of Syk. This plasmid DNA was introduced into competent cells, DH10BAC, contained in the Baculovirus Expression System to prepare DNA of recombinant virus. Thereafter, the recombinant virus (culture supernatant) was obtained by transfection of the DNA of recombinant virus into Sf-9 cells (ATCC).

The Sf-9 cells infected with this recombinant virus were recovered and lysed using a lysis buffer containing 1% Triton X-100. After centrifugation of the soluble fraction, TALON resin (CLONTECH) was added to the supernatant to allow the His-tag fused Syk protein to be adsorbed by the resin. After several times of washing of the resin, the His-tag fused Syk protein was eluted with a E buffer containing imidazole.

2) Preparation of Band 3 Peptide:

A peptide of 18 amino acid residues (MEELQDDYEDMMEENLEQ) containing Tyr-8 of human erythrocyte Band 3 (Harrison, M. L. et al., *J. Biol. Chem.*, 269: 955–959 (1994)) was synthesized using a peptide synthesizer. Using a biotinylation kit manufactured by Pierce, the N-terminal of the peptide under a resin-linked condition was biotinylated, and purification was carried out using an HPLC.

3) Measurement of Syk Tyrosine Kinase Activity Using an SPA System:

SPA (Scintillation Proximity Assay) is a system developed by Amersham making use of a phenomenon in which scintillation occurs when a molecule having a radioactivity is in the proximity of (linked to) the surface of plastic beads having a scintillant included therein. These beads are coated in advance with streptoavidin to which the biotin moiety of substrate peptide is bound.

A 2 µl portion of DMSO solution of each compound to be tested (final DMSO concentration, 4%) was added to each well containing 50 µl of a reaction solution (composition: 0.2 µg Syk, 50 mM Tris-HCl (pH 8), 10 mM $MgCl_2$, 50 mM NaCl, 1 mM DTT, 0.4 µM Band 3 peptide and 0.1 µCi [$\gamma$-$^{33}$P]ATP (10 mCi/ml, Amersham)). This was prepared in OptiPlate™ (PACKARD) and allowed to stand at room temperature (20 to 25° C.) for 1 hour to effect tyrosine phosphorylation.

The reaction was terminated by adding PBS containing 0.25 mg SPA beads, 50 µM ATP, 5 mM EDTA and 1% Triton X-100 (reaction termination solution) in an amount of 150 µl per well.

The plate was sealed, stirred, allowed to stand at room temperature for 15 minutes and then centrifuged at 1,500 rpm for 3 minutes to effect precipitation of the SPA beads. Radioactivity of each well was measured using TOP COUNT (PACKARD), and the tyrosine phosphorylation activity by Syk was calculated.

4) Results:

The following compounds of the present invention showed an inhibition activity of 0.1 µM or less as $IC_{50}$ value upon Syk tyrosine kinase. 2-(2-Aminoethylamino)-4-(3-methylanilino)pyrimidine-5-carboxamide, 2-(2-aminoethylamino)-4-(3-trifluoromethylanilino)pyrimidine-5-carboxamide, 2-(4-aminobutylamino)-4-(3-trifluoromethylanilino)pyrimidine-5-carboxamide, 2-(2-aminoethylamino)-4-(3-bromoanilino)pyrimidine-5-carboxamide, 2-(2-aminoethylamino)-4-(3-nitroanilino)pyrimidine-5-carboxamide, 2-(2-aminoethylamino)-4-(3,5-dimethylanilino)pyrimidine-5-carboxamide, 2-(2-aminoethylamino)-4-(2-naphthylamino)pyrimidine-5-carboxamide, 2-(cis-2-aminocyclohexylamino)-4-(3-methylanilino)pyrimidine-5-carboxamide, 2-(cis-2-aminocyclohexylamino)-4-(3-bromoanilino)pyriznidine-5-carboxamide, 2-(cis-2-aminocyclohexylamino)-4-(3,5-dichloroanilino)pyrimidine-5-carboxamide and 2-(cis-2-aminocyclohexylamino)-4-(3,4,5-trimethoxyanilino) pyrimidine-5-carboxamide.

2. 5-HT Release Test

This was carried out in accordance with the method reported by Collado-Escobar et al. (Collado-Escobar, D et al. *J. Immunol.*, 144: 3449–3457 (1990)).

The compound of the present invention excellently inhibited release of 5-HT.

3. Mouse Passive Cutaneous Anaphylaxis (PCA) Test

Male ICR (CD-1) mice of 5 weeks age were sensitized by subcutaneously injecting 10 µl of anti-dinitrophenyl-IgE (DNP-IgE) (1,000 times dilution of a partially purified preparation of ascites of Balb/c mouse to which a DNP-IgE producing hybridoma had been administered by intraperitoneal injection) under the right ear pinna while w lightly anesthetizing with ether. After 24 hours of the sensitization, 200 μl of 0.5% Evans blue solution containing 50 μg of DNP-conjugated bovine serum albumin was intravenously administered, and then each mouse was sacrificed by exsanguination 30 minutes thereafter to isolate both ears. Each test compound or the vehicle alone as a control was subcutaneously administered 30 minutes before the antigen challenge. The dye in the tissues was extracted with formamide and colorimetrically determined at 620 nm. A value obtained by subtracting the dye content of the left ear from the dye content of the right ear was used as the amount of dye leaked into the tissues by the PCA reaction.

The PCA inhibition ratio by the test compound was calculated based on the following equation. In the formula, CA: amount of the dye leaked into the sensitized right ear at the time of the administration of the vehicle alone, CB: amount of the dye leaked into the un-sensitized left ear at the time of the administration of the vehicle alone, XA: amount of the dye leaked into the sensitized right ear at the time of the administration of the compound to be tested, and XB: amount of the dye leaked into the un-sensitized left ear at the time of the administration of the compound to be tested.
Inhibition ratio (%)={(CA−CB)−(XA−XB)}×100/(CA−CB)

The compounds of the present invention excellently suppressed PCA reaction.

The pharmaceutical composition which contains one or two or more of the compounds represented by the general formula (I) or salts thereof as the active ingredient can be prepared by generally used methods using pharmaceutical carriers, fillers and the like which are generally used in this field. Its administration form may be either oral administration by tablets, pills, capsules, granules, powders, liquids and the like, or parenteral administration by intravenous, intramuscular and the like injections, suppositories, eye drops, eye ointments, percutaneous liquids, ointments, percutaneous adhesive preparations, transmucosal liquids, transmucosal adhesive preparations, inhalations and the like.

The solid composition for use in the oral administration according to the invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, aluminum magnesium silicate. In the usual way, the composition may contain other additives than the inert diluent, such as a lubricant (e.g., magnesium stearate or the like), a disintegrating agent (e.g., calcium cellulose glycolate or the like), a stabilizing agent (e.g., lactose or the like) and a solubilization assisting agent (e.g., glutamic acid, aspartic acid or the like). If necessary, tablets or pills may be coated with a film of a sugar coating, gastric or enteric substance such as sucrose, gelatin, hydroxypropylcellulose, hydroxypropylmethylcellulose phthalate or the like.

The liquid composition for oral administration use includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing agent, a moistening agent, a suspending agent and the like, as well as sweeteners, flavors, aromatics and antiseptics.

The injections for parenteral administration use include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil such as olive oil, alcohols such as ethanol, polysorbate 80 (trade name) and the like. Such a composition may further contain auxiliary agents such as a tonicity agent, an antiseptic, a moistening agent, an emulsifying agent, a dispersing agent, a stabilizing agent (e.g., lactose) and a solubilization assisting agent (e.g., glutamic acid or aspartic acid). These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

The transmucosal preparations such as transnasal preparations are in the solid, liquid or semisolid form and can be produced by known methods. For example, they are formed into a solid, liquid or semisolid state by optionally adding known pH adjusting agents, antiseptics, thickeners, excipients and the like. The transnasal preparations are administered using generally used sprayers, nasal drops containers, tubes, nasal cavity insertion tools and the like.

In the case of oral administration, the suitable daily dose is generally from about 0.001 to 100 mg/kg body weight, preferably from 0.1 to 10 mg/kg, which is administered in one portion or by dividing into two to four doses. In the case of intravenous injection, the suitable daily dose is from about 0.0001 to 10 mg/kg body weight, which is administered in one portion or by dividing into several doses. In the case of transmucosal preparations, a dose of from about 0.001 to 10 mg/kg body weight is administered once a day or by dividing into several doses. The dose is optionally decided by taking into consideration symptoms, age, sex and the like of each patient.

BEST MODE FOR CARRYING OUT THE INVENTION

The following describes the present invention further in detail based on Examples. Compounds of the present invention are not limited to the compounds described in the following Examples. In this connection, methods for the production of starting compounds to be used in the Examples are described as Reference Examples.

REFERENCE EXAMPLE 1

Ethyl 2,4-dichloropyrimidine-5-carboxylate was allowed to react with p-toluidine at room temperature in acetonitrile in the presence of diisopropylethylamine, thereby obtaining ethyl 2-chloro-4-(4-methylanilino)pyrimidine-5-carboxylate (light yellow powder).

REFERENCE EXAMPLE 2

4- (3 ,5-Dichloroanilino)-2-methylsulfanylpyrimidine-5-carbonitrile was allowed to react with cis-1,2-cyclohexanediamine under heat reflux in toluene to obtain 2-(cis-2-aminohexylamino)-4-(3,5-dichloroanilino)pyrimidine-5-carbonitrile (colorless solid).

REFERENCE EXAMPLE 3

In ethanol in which sodium had been dissolved, ethyl 3-ethoxy-2-[(3-methoxyphenyl)acetyl]acrylate and methyl-isothiourea sulfate were reacted under heat reflux to obtain ethyl 2-methylsulfanyl-4-(3-methoxybenzyl)pyrimidine-5-carboxylate (yellow oil).

REFERENCE EXAMPLE 4

N-(2-Hydroxyethyl)phthalimide was treated with lithium hydride in DMF and then allowed to react with ethyl 2-chloro-4-(3-methylanilino)pyrimidine-5-carboxylate at 80° C., thereby obtaining ethyl 2-[2-(1,3-dioxo-2,3-dihydroisoindol-2-yl)ethyl]amino-4-(3-methylanilino)pyrimidine-5-carboxylate (green crystals).

REFERENCE EXAMPLE 5

Ethyl 2-chloro-4-(4-methylanilino)-pyrimidine-5-carboxylate was treated with 1 M sodium hydroxide aqueous solution in THF at room temperature, thereby obtaining 2-chloro-4-(4-methylanilino)pyrimidine-5-carboxylic acid (light yellow powder).

REFERENCE EXAMPLE 6

2-Chloro-4-(4-methylanilino)pyrimidine-5-carboxylic acid was treated with HOBt and WSC-HCl in dichloroethane and then, under ice-cooling, allowed to undergo the reaction by adding 0.5 M ammonia-1,4-dioxane solution to obtain 2-(benzotriazol-1-yloxy)-4-(4-methylanilino) pyrimidine-5-carboxamide (light yellow powder).

REFERENCE EXAMPLE 7

2-(Benzotriazol-1-yloxy)-4-(4-methylanilino)pyrimidine-5-carboxamide and tert-butyl ester of 4-aminobenzylcarbamic acid were allowed to undergo the reaction in toluene under heat reflux, thereby obtaining tert-butyl ester of {4-[5-carbamoyl-4-(3-methylanilino) pyrimidin-2-ylamino]benzyl}carbamic acid (yellow solid).

REFERENCE EXAMPLE 8

Rink Amide AM resin formed into an amino compound (by removing Fmoc protecting group through piperazine treatment) was added to 2-chloro-4-(3-methylanilino) pyrimidine-5-carboxylic acid, and then a mixed solvent of dichloromethane and DMF was added thereto. Then, DIPC was added and the mixture was stirred at room temperature for 5 hours. The resin was collected by filtration and washed with dichloromethane, DMF, THF and methanol in that order. The same series of washing was repeated again, and then finally washed with diethyl ether. The resin was dried under a reduced pressure, thereby obtaining 2-chloro-4-(3-methylanilino)pyrimidine-5-carboxamide (resin) adhered to the resin via the nitrogen atom of the amide moiety.

In the following, using commercially available compounds or known compounds by the literature and the like, the compounds of Reference Examples 9 to 29 shown in Table 1 were produced in the same manner as described in Reference Example 1, and the compounds of Reference Examples 30 to 51 shown in Table 2 in the same manner as described in Reference Example 5, the compounds of Reference Examples 52 to 70 shown in Table 3 in the same manner as described in Reference Example 6 and the compound of Reference Example 71 shown in Table 3 in the same manner as described in Reference Example 7. Structures and physicochemical data of the compounds of Reference Examples 1 to 71 are shown in Tables 1 to 3.

EXAMPLE 1

A 3.0 ml portion of ethylenediamine was added to a mixture of 1.0 g of 2-(benzotriazol-1-yloxy)-4-(4-methylanilino)pyrimidine-5-carboxamide and 30 ml of acetonitrile, followed by stirring at room temperature for 1 hour and 40 minutes. Water was added to the reaction mixture, followed by extraction with a chloroform-isopropanol mixed solution. The resulting organic layer was dried over anhydrous sodium sulfate and concentrated under a reduced pressure and then the thus obtained residue was purified by silica gel column chromatography (eluting solvent; chloroform:methanol:aqueous ammonia) . By recrystallizing the thus obtained colorless solid from an ethyl acetate-ethanol mixed solvent, 471 mg of 2-(2-aminoethylamino)-4-(4-methylanilino)pyrimidine-5-carboxamide was obtained (colorless crystals).

EXAMPLE 2

A 128 mg portion of potassium carbonate and 350 µl of 31% hydrogen peroxide aqueous solution were added to a mixture of 350 mg of 2-(cis-2-aminohexylaminoy-4-(3,5-dichloroanilino)pyrimidine-5-carbonitrile with 5 ml of dimethyl sulfoxide, followed by stirring at room temperature for 2 hours. Distilled water was added to the reaction mixture, and the thus formed precipitate was collected by filtration. The filtered material was dissolved in ethyl acetate, 1 M hydrochloric acid aqueous solution was added thereto, and the thus formed precipitate was collected by filtration. By recrystallizing the filtered material from a mixed solvent of acetonitrile-water, 85 mg of 2-(cis-2-aminohexylamino)-4-(3,5-dichloroanilino)pyrimidine-5-carboxamide dihydrochloride was obtained (colorless crystals).

EXAMPLE 3

A 210 mg portion of HOBt and 320 mg of WSC·HCl were added to a mixture of 450 mg of 2-methyl-4-(3-trifluoromethylanilino)pyrimidine-5-carboxylic acid, 20 ml of DMF and dichloroethane, followed by stirring at room temperature for 2 hours. Then, 1.5 ml of 30% aqueous ammonia was added thereto and stirred for 1 hour. Water was added to the reaction mixture, followed by extraction with ethyl acetate. The organic layer was washed with water and saturated brine in that order. The organic layer was dried over anhydrous sodium sulfate and concentrated under a reduced pressure, and the thus obtained residue was purified by silica gel column chromatography (developing solvent: chloroform:methanol) and recrystallized from ethanol to obtain 280 mg of colorless crystals. A 12 ml portion of ethanol and 1.5 ml of 4 M hydrochloric acid-ethyl acetate were added to the thus obtained crystals, followed by stirring at room temperature for 1 hour. The solvent was evaporated under a reduced pressure, and the resulting colorless solid was recrystallized from a water-methanol mixed solvent to obtain 170 mg of 2-methyl-4-(3-trifluoromethylanilino) pyrimidine-5-carboxamide hydrochloride (colorless crystals).

EXAMPLE 4

Using CDI instead of WSC·HCl and HOBt as the condensing agent at the time of amidation, 2-(1H-imidazol-1-yl)-4-(3-trifluoromethylanilino)pyrimidine-5-carboxamide was obtained.

EXAMPLE 5

A 0.2 ml portion of hydrazine monohydrate was added to a mixture of 350 mg of 2-[2-(1,3-dioxo-2,3-dihydroisoindol-2-yl)ethyl]amino-4-(3-methylanilino)pyrimidine-5-carboxamide with 10 ml of ethanol, followed by heating under reflux for 4 hours. The reaction mixture was concentrated under a reduced pressure. A chloroform-methanol mixed solution was added to the thus obtained residue, followed by washing with water, 1 M sodium hydroxide aqueous solution and saturated brine. The organic layer was dried over anhydrous magnesium sulfate and concentrated under a reduced pressure, and the resulting residue was recrystallized from ethanol to obtain 140 mg of 2-(2-aminoethoxy)-4-(3-methylanilino)pyrimidine-5-carboxamide (colorless crystals).

EXAMPLE 6

A 100 mg portion of 10% palladium-carbon powder was added to a mixture of 869 mg of 2-(2-aminoethylamino)-4-(3-benzyloxyanilino)pyrimidine-5-carboxamide with THF, methanol and DMF, followed by stirring at room temperature for 3 days in an atmosphere of hydrogen under ordinary pressure. The reaction mixture was filtered, and the filtrate was concentrated under a reduced pressure. By Ad:. recrystallizing the resulting residue from an ethyl acetate-methanol mixed solvent, 217 mg of 2-(2-aminoethylamino)-4-(3-hydroxyanilino)pyrimidine-5-carboxamide was obtained (light brown solid).

EXAMPLE 7

A 12 ml portion of 4 M hydrochloric acid-dioxane solution was added to a mixture of 580 mg of tert-butyl ester of 3-[2-(2-aminoethylamino)-5-carbamoylpyrimidin-4-ylamino]benzoic acid with 6 ml of methanol and 6 ml of water and stirred at 80° C. for 1 hour. The organic solvent was evaporated from the reaction mixture under a reduced pressure, and the thus formed precipitate was collected by filtration. After adding methanol and water, the mixture was heated. The insoluble matter was removed by filtration and then the mother liquid was concentrated under a reduced pressure. By recrystallizing the resulting residue from a mixed solvent of methanol and water, 59 mg of 3-[2-(2-aminoethylamino)-5-carbamoylpyrimidin-4-ylamino]benzoic acid dihydrochloride was obtained (colorless crystals).

EXAMPLE 8

A 4 ml portion of 4 M hydrochloric acid-dioxane solution was added to 183 mg of tert-butyl ester of {4-[5-carbamoyl-4-(3-methylanilino)pyrimidin-2-ylamino]benzyl}carbamic acid, followed by stirring at room temperature for 16 hours. Water and ethyl acetate were added to the reaction mixture, the thus formed insoluble matter was removed by filtration and the filtrate was alkalified by adding 1 M sodium hydroxide aqueous solution. After extraction with ethyl acetate, the organic layer was washed with saturated brine and dried over anhydrous magnesium sulfate. The residue concentrated under a reduced pressure was recrystallized from a mixed solvent of ethyl acetate and n-hexane, thereby obtaining 44 mg of 2-(4-aminomethylanilino)-4-(3-methylanilino)pyrimidine-5-carboxamide (light yellow crystals).

EXAMPLE 9

An 87 µl portion of acetyl chloride and ⁻170 µl of triethylamine were added to a mixture of 318 mg of 2-(2-aminoethylamino)-4-(3-methylanilino)pyrimidine-5-carboxamide and 20 ml of ethyl acetate, followed by stirring at room temperature for 30 minutes. Water and THF were added to the reaction mixture, followed by extraction with ethyl acetate. The organic layer was washed with saturated brine, dried over anhydrous magnesium sulfate and then concentrated under a reduced pressure. The resulting residue was recrystallized from a mixed solvent of THF and ethyl acetate, thereby obtaining 198 mg of 2-[(2-acetylaminoethyl)amino]-4-(3-methylanilino)pyrimidine-5-carboxamide (colorless crystals).

EXAMPLE 10

A mixture of 350 mg of N-tert-butoxycarbonylglycine, 270 mg of HOBt, 384 mg of WSC·HCl and 10 ml of 1,2-dichloroethane was stirred at room temperature for 30 minutes, 2-(2-aminoacetyl)amino-4-(3-trifluoromethylanilino)pyrimidine-5-carboxamide was added, followed by stirring overnight at room temperature. Water was added to the reaction mixture, followed by extraction with a chloroform-isopropanol mixed solution. The combined organic layer was dried over anhydrous magnesium sulfate and concentrated under a reduced pressure to obtain 2-[2-tert-(butoxycarbonylamino)acetylamino]-4-(3-trifluoromethylanilino)pyrimidine-5-carboxamide. This was dissolved in 5 ml of methanol, and 10 ml of 4⁻M hydrochloric acid-ethyl acetate solution was added, followed by stirring at room temperature for 2 hours. Methanol and ethyl acetate were added to the reaction mixture, and the mixture was washed with saturated sodium bicarbonate aqueous solution and saturated brine, dried over anhydrous sodium sulfate and then concentrated under a reduced pressure. The resulting residue was purified by silica gel column chromatography (eluting solvent; chloroform:methanol:aqueous ammonia), thereby obtaining 70 mg of 2-(2-aminoacetylamino)-4-(3-trifluoromethylanilino)pyrimidine-5-carboxamide (colorless crystals).

EXAMPLE 11

A 114 µl portion of methanesulfonyl chloride and 205 µl of triethylamine were added to a mixture of 382 mg of 2-(2-aminoethylamino)-4-(3-methylanilino)pyrimidine-5-carboxamide with 10 ml of ethyl acetate, followed by stirring at room temperature for 3.5 hours. The reaction mixture was washed with water and saturated brine, and then the organic layer was dried over anhydrous magnesium sulfate. This was concentrated under a reduced pressure and the resulting residue was recrystallized from a mixed solvent of methanol and ethyl acetate to obtain 210 mg of 2-{[2-(methanesulfonylamino)ethyl]amino}-4-(3-methylanilino)pyrimidine-5-carboxamide (colorless crystals).

EXAMPLE 12

A 508 mg portion of 3,5-dimethylpyrazole-1-carboxamidine nitrate and 876 µl of diisopropylethylamine were added to a mixture of 328 mg of 2-(2-aminoethylamino)-4-(3-methylanilino)pyrimidine-5-carboxamide and THF, followed by stirring at 60° C. for one week. Water and ethyl acetate were added to the reaction mixture, and the water layer was concentrated under a reduced pressure. The resulting residue was washed with a mixed solution of methanol and ethyl acetate and then recrystallized from a mixed solvent of methanol and water to obtain 200 mg of 2-[(2-guanidinoethyl)amino]-4-(3-methylanilino)pyrimidine-5-carboxamide nitrate as colorless crystals.

EXAMPLE 13

A 135 mg portion of HOBt and 192 mg of WSC·HCl were added to a mixture of 195 mg of (Z)-3-[2-(acetoxy)phenyl]acrylic acid and 10 ml of dichloroethane, followed by stirring for 20 minutes under ice-cooling. Then, 2 ml of DMF solution containing 340 mg of 2-(cis-2-aminocyclohexylamino)-4-(3-methylanilino)pyrimidine-5-carboxamide was added, followed by stirring at room temperature for 2 hours. Water was added to the reaction mixture, followed by extraction with ethyl acetate. The organic layer was dried over anhydrous sodium sulfate and concentrated under a reduced pressure. The resulting residue was purified by silica gel column chromatography (eluting solvent; chloroform:methanel) and then the thus obtained colorless solid was recrystallized from ethyl acetate, thereby obtaining 98 mg of 2-{(Z)-2-[(cis-2-{[5-carbamoyl-4-(3-methylanilino)pyrimidin-2-yl]amino}cyclohexyl)carbamoyl]vinyl}phenyl acetate (colorless crystals).

EXAMPLE 14

A 147 mg portion of potassium cyanate and 450 µl of 4 M hydrochloric acid-dioxane solution were added to a mixture of 312 mg of 2-(2-aminoethylamino)-4-(3-methylanilino)pyrimidine-5-carboxamide and 3 ml of water and 3 ml of 1,4-dioxane, followed by stirring at room temperature for 1 day. The reaction mixture was alkalified by adding 1 M sodium hydroxide aqueous solution, and the thus formed precipitate was collected by filtration. The filtered material was washed by stirring it in methanol while heating and then collected by filtration to obtain 212 mg of 4-(3-methylanilino)-2-[(2-ureidoethyl)amino]pyrimidine-5-carboxamide (colorless solid).

Solid Phase Synthesis Method 100 mg (equivalent to 40 µM) portions of 2-chloro-4-(3-methylanilino)pyrimidine-5-carboxamide (resin) adhered to the resin via the nitrogen atom of the amide moiety, prepared in the Reference Example, were respectively added into 96 wells of the reaction vessel of a synthesizing machine (ACT496MOS manufactured by Advanced ChemTech). Thereafter, N-methylpyrrolidone 0.5 M solution of a corresponding amine compound in 1.0 ml portions and N-methylpyrrolidone 2.5 M solution of diisopropylethylamine in 200 µl portions were dispensed into respective wells and 12 hours of shaking was carried out at 100° C. After removal of the reaction solution by filtration, respective resins were washed with DMF twice and then with dichloromethane, DMF, THF, methanol and THF in that order. To respective resins were added 4 ml of 40% trifluoroacetic acid solution in dichloromethane, and the mixtures were shaken at room temperature for 5 minutes. Respective resins were removed by filtration, and the reaction mixtures were collected. Respective solvents were evaporated under a reduced pressure to obtain 2-(substituted amino)-4-(3-methylanilino)pyrimidine-5-carboxamide compounds. Identification of the compounds was carried out based on mass spectrometry and retention time of HPLC, and the area ratio of HPLC was used as the purity of compound.

The compounds of Examples 15 to 47 shown in Tables 4 and 5 were synthesized in the same manner as described in Example 1, the compounds of Examples 48 to 50 shown in Table 5 were synthesized in the same manner as described in Example 3, and the compounds of Examples 51 to 60 were synthesized by the solid phase synthesis method. Structures, production methods and physicochemical data of the example compounds 1 to 60 are shown in Tables 4 and 5.

Also, structures of other compounds of the present invention are shown in Tables 6 to 9. These compounds can be easily synthesized by the aforementioned production methods and the methods described in the Examples, as well as the methods which are obvious to those skilled in the art or modified methods thereof.

The following abbreviations are used in the tables. Also, the number before each substituent group indicates the substitution position, and plural numbers indicates plural substitutions. For example, 3,5-Me indicates 3,5-dimethyl.

Rex: Reference Example number; Ex: Example number; Cmp: compound number; Syn: production method (A to H: produced in the same manner as Examples 1, 2, 3, 10, 11, 12, 14 and 51, respectively; C', D': respectively produced in the same manner as Examples 3 and 4, followed by deprotection); Sal: salt (Fu: fumarate; Ox: oxalate; blank space: free form; regarding the number before each acid component, 2HCl, for example, indicates dihydrochloride, and the absence of a number means 1); Dat: physicochemical data (F: FAB-MS $(M+H)^+$; FN: FAB-MS $(M-H)^-$; E: EI-MS; M: melting point (° C.); dec: decomposition); Ph: phenyl; Bn: benzyl; Me: methyl; Et: ethyl; Pr: propyl; iPr: 2-propyl; Bu: butyl; tBu: tert-butyl; Bt: benzotriazol-1-yl; Ac: acetyl; Boc: tBuO-CO. Also, a compound in which $R^b$ is 2,3-$(CH)_4$ forms a 2-naphthyl group together with the adjacent benzene ring.

TABLE 1

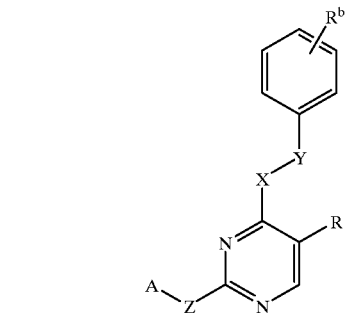

| Rex | A—Z | R | X—Y | $R^b$ | Dat |
|---|---|---|---|---|---|
| 1 | Cl | $CO_2Et$ | NH | 4-Me | F 292 |
| 2 | 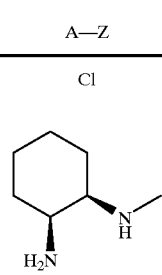 | CN | NH | 3,5-Cl | F 377, 379 |
| 3 | MeS | $CO_2Et$ | $CH_2$ | 3-OMe | F 319 |

TABLE 1-continued

| Rex | A—Z | R | X—Y | R$^b$ | Dat |
|---|---|---|---|---|---|
| 4 | (phthalimide-N-CH$_2$CH$_2$-OMe) | CO$_2$Et | NH | 3-Me | F 447 |
| 9 | Cl | CO$_2$Et | NH | 3-Me | F 292 |
| 10 | Cl | CO$_2$Et | NH | 2-Me | F 292 |
| 11 | Cl | CO$_2$Et | NH | 3-CF$_3$ | F 346 |
| 12 | Cl | CO$_2$Et | NH | 3-CN | F 303 |
| 13 | Cl | CO$_2$Et | NH | 3-OMe | F 308 |
| 14 | Cl | CO$_2$Et | NH—CH$_2$ | 3-CF$_3$ | F 360 |
| 15 | Cl | CO$_2$Et | S | 3-CF$_3$ | F 363 |
| 16 | Cl | CO$_2$Et | NH | 3-Br | F 358 |
| 17 | Cl | CO$_2$Et | NH | 2,3-(CH$_2$)$_4$ | F 332 |
| 18 | Cl | CO$_2$Et | NH | 3,4-(CH$_2$)$_3$ | F 318 |
| 19 | Cl | CO$_2$Et | NH | 3,5-Me | FN 304 |
| 20 | Cl | CO$_2$Et | NH | 2,3-(CH)$_4$ | F 328 |
| 21 | MeS | CO$_2$Et | NH | 3-OBn | F 396 |
| 22 | MeS | CO$_2$Et | NH | 3-Boc | F 390 |
| 23 | MeS | CO$_2$Et | NH | 3-NO$_2$ | F 335 |
| 24 | MeS | CO$_2$Et | NH | 3-CF$_3$ | F 358 |
| 25 | MeS | CO$_2$Et | N(Me) | 3-CF$_3$ | |
| 26 | Me | CO$_2$Et | NH | 3-CF$_3$ | F 326 |
| 27 | Ph | CO$_2$Et | NH | 3-CF$_3$ | F 388 |
| 28 | AcHN | CO$_2$Et | NH | 3-CF$_3$ | F 369 |
| 29 | MeS | CN | NH | 3,5-Cl | F 311 |

TABLE 2

| Rex | A—Z | X—Y | R$^b$ | Dat |
|---|---|---|---|---|
| 5 | Cl | NH | 4-Me | FN 262 |
| 30 | Cl | NH | 3-Me | F 264 |
| 31 | Cl | NH | 2-Me | FN 262 |
| 32 | Cl | NH | 5-CF$_3$ | F 318 |
| 33 | Cl | NH | 3-CN | FN 273 |
| 34 | Cl | NH | 3-OMe | FN 278 |
| 35 | Cl | NH—CH$_2$ | 3-CF$_3$ | F 332 |

TABLE 2-continued

*(Structure: phenyl with R$^b$ — X—Y — pyrimidine with CO$_2$H at 5-position and A—Z at 2-position)*

| Rex | A—Z | X—Y | R$^b$ | Dat |
|---|---|---|---|---|
| 36 | Cl | S | 3-CF$_3$ | F 299 |
| 37 | Cl | NH | 3-Br | FN 328 |
| 38 | Cl | NH | 2,3-(CH$_2$)$_4$ | F 304 |
| 39 | Cl | NH | 3,4-(CH$_2$)$_3$ | F 290 |
| 40 | Cl | NH | 3,5-Me | FN 276 |
| 41 | Cl | NH | 2,3-(CH)$_4$ | F 300 |
| 42 | MeS | NH | 3-OBn | F 368 |
| 43 | MeS | NH | 3-Boc | F 362 |
| 44 | MeS | NH | 3-NO$_2$ | F 307 |
| 45 | MeS | NH | 3-CF$_3$ | F 330 |
| 46 | MeS | N(Me) | 3-CF$_3$ | F 344 |
| 47 | Me | NH | 3-CF$_3$ | F 298 |
| 48 | Ph | NH | 3-CF$_3$ | F 360 |
| 49 | H$_2$N | NH | 3-CF$_3$ | F 299 |
| 50 | MeS | CH$_2$ | 3-OMe | F 291 |
| 51 | *(phthalimido-CH$_2$CH$_2$-OMe)* | NH | 3-Me | F 419 |

TABLE 3

*(Structure: phenyl with R$^b$ — X—Y — pyrimidine with CONH$_2$ at 5-position and A—Z at 2-position)*

| Rex | A—Z | X—Y | R$^b$ | Dat |
|---|---|---|---|---|
| 6 | BtO | NH | 4-Me | F 362 |
| 7 | Boc-NH-CH$_2$-C$_6$H$_4$-NH(Me)- | NH | 3-Me | F 449 |
| 52 | BtO | NH | 3-Me | F 362 |
| 53 | BtO | NH | 2-Me | F 362 |
| 54 | BtO | NH | 3-CF$_3$ | F 416 |
| 55 | BtO | NH | 3-CN | F 373 |

TABLE 3-continued
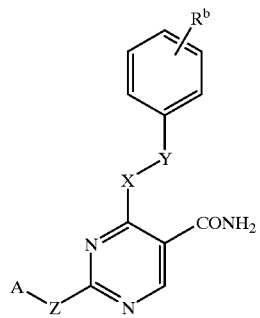
| Rex | A—Z | X—Y | R$^b$ | Dat |
|---|---|---|---|---|
| 56 | BtO | NH | 3-OMe | F 378 |
| 57 | BtO | NH—CH$_2$ | 3-CF$_3$ | F 430 |
| 58 | BtO | S | 3-CF$_3$ | FN 431 |
| 59 | BtO | NH | 3-Br | FN 424 |
| 60 | BtO | NH | 2,3-(CH$_2$)$_4$ | F 402 |
| 61 | BtO | NH | 3,4-(CH$_2$)$_3$ | F 388 |
| 62 | BtO | NH | 3,5-Me | FN 374 |
| 63 | BtO | NH | 2,3-(CH)$_4$ | |
| 64 | MeS | NH | 3-OBn | F 367 |
| 65 | MeS | NH | 3-Boc | F 361 |
| 66 | MeS | NH | 3-NO$_2$ | F 306 |
| 67 | MeS | NH | 3-CF$_3$ | F 329 |
| 68 | MeS | N(Me) | 3-CF$_3$ | F 343 |
| 69 | MeS | CH$_2$ | 3-OMe | F 290 |
| 70 | 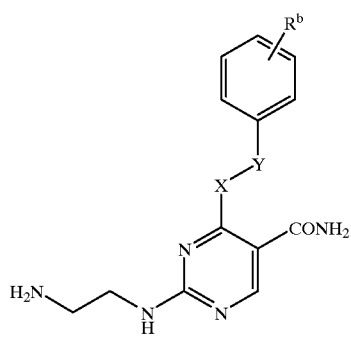 | NH | 3-Me | F 418 |
| 71 | 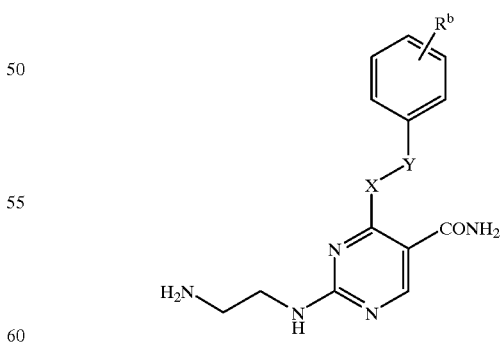 | NH | 3-Me | F 458 |
TABLE 4
| Ex | Syn | X—Y | R$^b$ | Sal | Dat |
|---|---|---|---|---|---|
| 1 | A | NH | 4-Me | | F 287, M 191–193 |
| 6 | C' | NH | 3-HO | | F 289, M 203–207 (dec) |
| 7 | C' | NH | 3-CO$_2$H | 2HCl | F 317, M 285–290 |
| 15 | A | NH | 3-Me | | F 287, M 185–188 |
| 16 | A | NH | 2-Me | | F 287, M 185–187 |
| 17 | A | NH | 3-CF$_3$ | 2HCl | F 341, M 270–172 (dec) |
| 18 | A | NH | 3-CN | | F 298, M 192–194 |
| 19 | A | NH | 3-MeO | | F 303, M 142–145 |

TABLE 4-continued
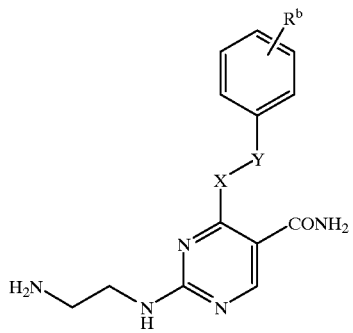
| Ex | Syn | X—Y | R^b | Sal | Dat |
|----|-----|------|------|-----|-----|
| 20 | A | NH—CH$_3$ | 3-CF$_3$ | | F 355, M 193–196 |
| 21 | A | S | 3-CF$_3$ | | F 358 |
| 22 | A | NH | 3-Br | | F 351, M 194–196 |
| 23 | A | NH | 2,3-(CH$_2$)$_4$ | | F 327 |
| 24 | A | NH | 3,4-(CH$_2$)$_3$ | | F 313 |
| 25 | A | NH | 3,5-Me | | F 301 |
TABLE 4-continued
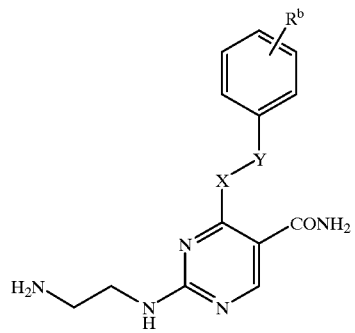
| Ex | Syn | X—Y | R^b | Sal | Dat |
|----|-----|------|------|-----|-----|
| 26 | A | NH | 2,3-(CH)$_4$ | | F 323 |
| 41 | A | NH | 3-BnO | | F 379, M 192–194 |
| 42 | A | NH | 3-NO$_2$ | | F 318, M 210–214 (dec) |
| 43 | A | CH$_2$ | 3-MeO | | F 302, M 127–129 |
| 44 | A | N(Me) | 3-CF$_3$ | Ox | F 355, M 223–225 |
TABLE 5
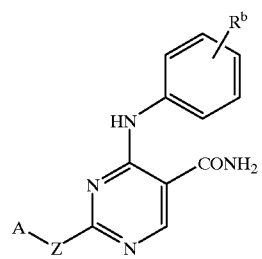
| Ex | Syn | A—Z— | R^b | Sal | Dat |
|----|-----|------|------|-----|-----|
| 2 | B | 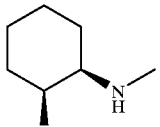 | 3,5-Cl | 2HCl | F 395, M 285–300 (dec) |
| 3 | C | Me- | 3-CF$_3$ | HCl | F 297, M 254–255 (dec) |
| 4 | C | 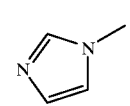 | 3-Me | | F 295, M 240–242 |
| 5 | C' |  | 3-Me | | F 288, M 155–157 |
| 8 | C' | 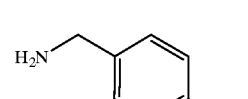 | 3-Me | | F 349, M 197–203 |
| 9 | D | 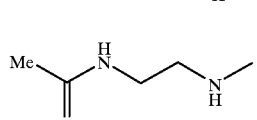 | 3-Me | | F 329, M 250–253 |

TABLE 5-continued

| Ex | Syn | A—Z— | R^b | Sal | Dat |
|---|---|---|---|---|---|
| 10 | D' | H₂N-CH₂-C(O)-NH-Me | 3-CF₃ | | F 355 |
| 11 | E | Me-S(O)₂-NH-CH₂CH₂-NH-Me | 3-Me | | F 365, M 202–204 |
| 12 | F | H₂N-C(=NH)-NH-CH₂CH₂-NH-Me | 3-Me | HNO₃ | F 329, M 254–257 |
| 13 | D | 2-(AcO)-C₆H₄-CH=CH-C(O)-NH-cyclohexyl-NH-Me | 3-Me | | F 529, M 171–173 |
| 14 | G | H₂N-C(O)-NH-CH₂CH₂-NH-Me | 3-Me | | F 330, M 249–250 |
| 27 | A | Me₂N-CH₂CH₂-NH- | 3-CF₃ | | F 369, M 185–187 |
| 28 | A | Me₂N-CH₂CH₂-N(Me)- | 3-CF₃ | | F 383, M 153–157 |
| 29 | A | 4-methylpiperazin-1-yl | 3-CF₃ | | F 367, M 207–209 |
| 30 | A | morpholino-CH₂CH₂-NH- | 3-CF₃ | 0.5Fu | F 411, M 222–224 (dec) |

TABLE 5-continued

[Structure: pyrimidine with 4-NH-phenyl(R^b), 5-CONH2, 2-A-Z- substituent]

| Ex | Syn | A—Z— | R^b | Sal | Dat |
|---|---|---|---|---|---|
| 31 | A | H2N-(CH2)4-NH(Me) | 3-CF$_3$ | | F 369, M 198–200 |
| 32 | A | 4-H2N-C6H4-CH2-NH(Me) | 3-CF$_3$ | | FN 401, M 259 (dec) |
| 33 | A | MeNH-CH2CH2-NH(Me) | 3-CF$_3$ | | F 355, M 194–196 |
| 34 | A | (1R,2R)-2-aminocyclohexyl-NH(Me) | 3-Br | | F 405, M 204–206 |
| 35 | A | (1R,2R)-2-aminocyclohexyl-NH(Me) | 3-Me | | F 341, M 161–163 |
| 36 | A | HC≡C-CH2-NH(Me) | 3-Br | | F 348, M 217–220 (dec) |
| 37 | A | (1S,2S)-2-aminocyclohexyl-NH(Me) | 3-Me | | F 341, M 171–175 |
| 38 | A | (1R,2S)-1,2-diphenyl-2-amino-ethyl-NH(Me) | 3,5-Me | HCl | F 453, M 256–259 |
| 39 | A | 2-aminophenyl-NH(Me) | 3-Me | | F 335, M 220–224 |

TABLE 5-continued

| Ex | Syn | A—Z— | R^b | Sal | Dat |
|---|---|---|---|---|---|
| 40 | A | (2-hydroxyphenyl)-NH-Me | 3-Me | | F 336, M 220–223 |
| 45 | A | H$_2$N-CH(CH$_2$NH-)-C(O)-NH-Et | 3-Me | 2HCl | F 358, M 218–220 |
| 46 | A | HO-CH$_2$CH$_2$-NH- | 3-CF$_3$ | | F 342, M 216–219 |
| 47 | A | H$_2$N-CH$_2$CH$_2$CH$_2$-NH- | 3-CF$_3$ | | F 355, M 185–189 |
| 48 | C | Ph- | 3-CF$_3$ | | F 359, M 233–235 |
| 49 | C | H$_2$N— | 3-CF$_3$ | | F 298, M: 234–235 |
| 50 | C' | Et-NH-C(O)-CH(NH-)-CH$_2$NH$_2$ | 3-Me | 2HCl | F 358, M 206–209 (dec) |
| 51 | H | H$_2$N-CH(Me)-CH$_2$-NH- | 3-Me | | F 301 |
| 52 | H | HO-(4-phenyl)-CH$_2$CH$_2$-NH- | 3-Me | | F 364 |

TABLE 5-continued

| Ex | Syn | A—Z— | R$^b$ | Sal | Dat |
|---|---|---|---|---|---|
| 53 | H | (H$_2$N-CH$_2$-CH(S-CH$_2$-C$_6$H$_4$-OMe-p)-CH$_2$-NH-) | 3-Me | | F 453 |
| 54 | H | (H$_2$N-CH$_2$-(m-C$_6$H$_4$)-CH$_2$-NH-) | 3-Me | | F 363 |
| 55 | H | (H$_2$N-CH$_2$-CH(CO$_2$Me)-NH-) | 3-Me | | F 345 |
| 56 | H | (1-indanyl-NH-) | 3-Me | | F 360 |
| 57 | H | (2-pyridyl-CH$_2$-NH-) | 3-Me | | F 335 |
| 58 | H | (tetrahydrofuran-2-yl-CH$_2$-NH-) | 3-Me | | F 328 |
| 59 | H | (furan-2-yl-CH$_2$-NH-) | 3-Me | | F 324 |

TABLE 5-continued
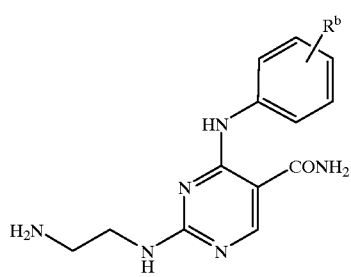
| Ex | Syn | A—Z— | R$^b$ | Sal | Dat |
|---|---|---|---|---|---|
| 60 | H | (thiophene-2-CH$_2$-NH-) | 3-Me | F | 340 |
TABLE 6
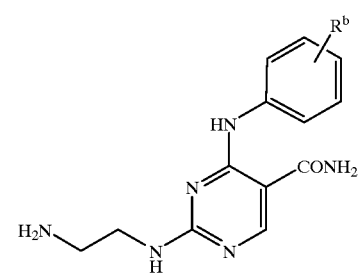
| Cmp | R$^b$ |
|---|---|
| 1 | 2-F |
| 2 | 3-F |
| 3 | 4-F |
| 4 | 2-Cl |
| 5 | 3-Cl |
| 6 | 4-Cl |
| 7 | 2-CH$_2$OH |
| 8 | 3-CH$_2$OH |
| 9 | 4-CH$_2$OH |
| 10 | 2-NH$_2$ |
| 11 | 3-NH$_2$ |
| 12 | 4-NH$_2$ |
| 13 | 2-Ac |
| 14 | 3-Ac |
| 15 | 4-Ac |
| 16 | 2-SMe |
| 17 | 3-SMe |
| 18 | 4-SMe |
| 19 | 2-OPh |
| 20 | 3-OPh |
| 21 | 4-OPh |
| 22 | 2-Et |
| 23 | 3-Et |
| 24 | 4-Et |
| 25 | 2-Pr |
| 26 | 3-Pr |
| 27 | 4-Pr |
| 28 | 2-Bu |
| 29 | 3-Bu |
| 30 | 4-Bu |
| 31 | 2-iPr |
| 32 | 3-iPr |
| 33 | 4-iPr |
| 34 | 2,3-OCH$_2$O |
TABLE 6-continued
| Cmp | R$^b$ |
|---|---|
| 35 | 3,4-OCH$_2$O |
| 36 | 3,4-(CH)$_4$ |
TABLE 7
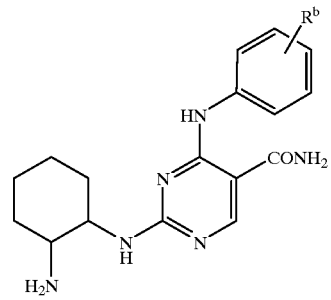
| Cmp | R$^b$ |
|---|---|
| 37 | 2-F |
| 38 | 3-F |
| 39 | 4-F |
| 40 | 2-Cl |
| 31 | 3-Cl |
| 42 | 4-Cl |
| 43 | 2-CH$_2$OH |
| 44 | 3-CH$_2$OH |
| 45 | 4-CH$_2$OH |
| 46 | 2-NH$_2$ |

TABLE 7-continued
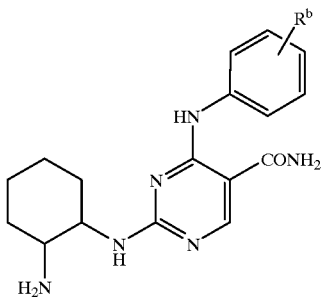
| Cmp | R$^b$ |
|---|---|
| 47 | 3-NH$_2$ |
| 48 | 4-NH$_2$ |
| 49 | 2-Ac |
| 50 | 3-Ac |
| 51 | 4-Ac |
| 52 | 2-SMe |
| 53 | 3-SMe |
| 54 | 4-SMe |
| 55 | 2-OPh |
| 56 | 3-OPh |
| 57 | 4-OPh |
| 58 | 2-Et |
| 59 | 3-Et |
| 60 | 4-Et |
TABLE 7-continued
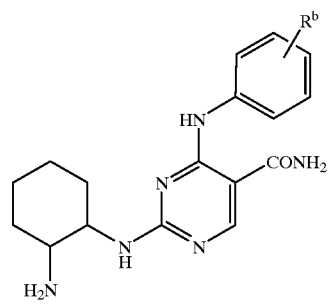
| Cmp | R$^b$ |
|---|---|
| 61 | 2-Pr |
| 62 | 3-Pr |
| 63 | 4-Pr |
| 64 | 2-Bu |
| 65 | 3-Bu |
| 66 | 4-Bu |
| 67 | 2-iPr |
| 68 | 3-iPr |
| 69 | 4-iPr |
| 70 | 2,3-OCH$_2$O |
| 71 | 3,4-OCH$_2$O |
| 72 | 3,4-(CH)$_4$ |
TABLE 8
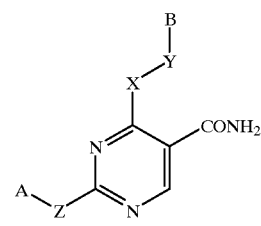
| Cmp | X—Y | A—Z | B |
|---|---|---|---|
| 73 | —NH— | H$_2$N‑CH$_2$CH$_2$‑NH— | 1-methylfluorenyl |
| 74 | | 2-aminocyclohexyl-NH(Me)— | |
| 75 | —NH— | H$_2$N‑CH$_2$CH$_2$‑NH— | methyldibenzofuranyl |

TABLE 8-continued
| Cmp | X—Y | A—Z | B |
|---|---|---|---|
| 76 | | 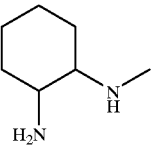 | |
| 77 | —NH— |  | 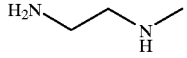 |
| 78 | | 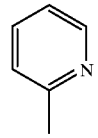 | |
| 79 | —NH— | 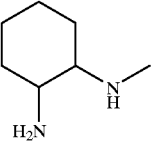 |  |
| 80 | | 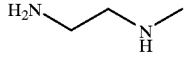 | |
| 81 | —NH— | 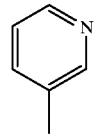 | 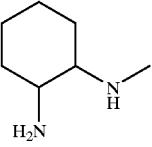 |
| 82 | |  | |
| 83 | —NH— | 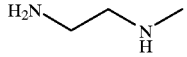 | 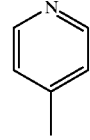 |

TABLE 8-continued
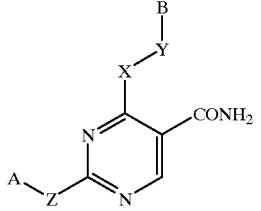
| Cmp | X—Y | A—Z | B |
|---|---|---|---|
| 84 | | 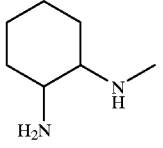 | |
| 85 | —NH— | 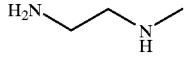 | 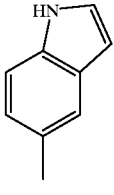 |
| 86 | | 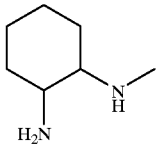 | |
| 87 | —NH— | 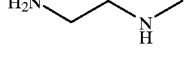 | 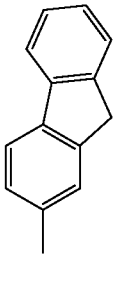 |
| 88 | | 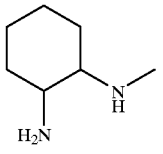 | |
| 89 | —NH— | 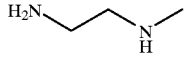 | 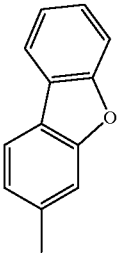 |

TABLE 8-continued

| Cmp | X—Y | A—Z | B |
|---|---|---|---|
| 90 | | 2-aminocyclohexyl-N(H)Me | |
| 91 | —NH— | H₂N-CH₂CH₂-N(H)- | 5-methylbenzothiazol-2-yl |
| 92 | | 2-aminocyclohexyl-N(H)Me | |
| 93 | —NH— | H₂N-CH₂CH₂-N(H)- | 5-methylthiophen-2-yl |
| 94 | | 2-aminocyclohexyl-N(H)Me | |
| 95 | —CH(OH)— | H₂N-CH₂CH₂-N(H)- | 3-methylphenyl |
| 96 | | 2-aminocyclohexyl-N(H)Me | |
| 97 | —CO— | H₂N-CH₂CH₂-N(H)- | 3-methylphenyl |

TABLE 8-continued

| Cmp | X—Y | A—Z | B |
|---|---|---|---|
| 98 |  | 2-aminocyclohexyl-N(H)methyl |  |
| 99 | —C(=NOH)— | H₂N-CH₂CH₂-N(H)- | 3-methylphenyl |
| 100 |  | 2-aminocyclohexyl-N(H)methyl |  |

TABLE 9

| Cmp | Rb | A—Z |
|---|---|---|
| 101 | Me | 2-aminocyclopentyl-N(H)methyl |
| 102 | Br |  |
| 103 | Cl |  |
| 104 | CF₃ |  |
| 105 | Me | 2-aminocycloheptyl-N(H)methyl |
| 106 | Br |  |
| 107 | Cl |  |
| 108 | CF₃ |  |
| 109 | Me | 3-aminophenyl-N(H)methyl |
| 110 | Br |  |
| 111 | Cl |  |
| 112 | CF₃ |  |
| 113 | Me | 4-aminophenyl-N(H)methyl |
| 114 | Br |  |
| 115 | Cl |  |
| 116 | CF₃ |  |

TABLE 9-continued

| Cmp | Rb | A—Z |
|---|---|---|
| 117 | Me | (3-aminomethyl-phenyl)-NHMe |
| 118 | Br | |
| 119 | Cl | |
| 120 | CF₃ | |
| 121 | Me | (2-aminomethyl-phenyl)-NHMe |
| 122 | Br | |
| 123 | Cl | |
| 124 | CF₃ | |
| 125 | Me | (4-aminoethyl-phenyl)-NHMe |
| 126 | Br | |
| 127 | Cl | |
| 128 | CF₃ | |
| 129 | Me | HONHC(O)-C₆H₄-NHMe |
| 130 | Br | |
| 131 | Cl | |
| 132 | CF₃ | |
| 133 | Me | HOOC-C₆H₄-NHMe |
| 134 | Br | |
| 135 | Cl | |
| 136 | CF₃ | |
| 137 | Me | AcOCH₂OC(O)NH-CH₂CH₂-NHMe |
| 138 | Br | |
| 139 | Cl | |
| 140 | CF₃ | |

TABLE 9-continued

| Cmp | Rb | A—Z |
|---|---|---|
| 141 | Me | AcOCH₂OC(O)NH-cyclohexyl-NHMe |
| 142 | Br | |
| 143 | Cl | |
| 144 | CF₃ | |
| 145 | Me | (4-methyl-2-oxo-1,3-dioxol-5-yl)methoxycarbonyl-NH-CH₂CH₂-NHMe |
| 146 | Br | |
| 147 | Cl | |
| 148 | CF₃ | |
| 149 | Me | (4-methyl-2-oxo-1,3-dioxol-5-yl)methoxycarbonyl-NH-cyclohexyl-NHMe |
| 150 | Br | |
| 151 | Cl | |
| 152 | CF₃ | |
| 153 | Me | (2-hydroxyphenyl)(phenyl)C=N-CH₂CH₂-NHMe |
| 154 | Br | |
| 155 | Cl | |
| 156 | CF₃ | |
| 157 | Me | (phenyl)(2-hydroxyphenyl)C=N-cyclohexyl-NHMe |
| 158 | Br | |
| 159 | Cl | |
| 160 | CF₃ | |

What is claimed is:

1. A pyrimidine-5-carboxamide derivative represented by a formula (I) or a salt thereof

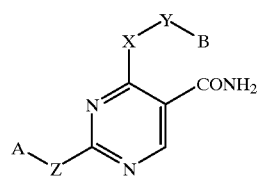
(I)

wherein each symbol has the following meaning;
- X: O; S; NR$^1$; CO; NR$^1$CO; CONR$^1$; C=N—OR$^1$ or a bond,
- Y: a lower alkylene group which may be substituted by OR$^1$ or —NHR$^1$; or a bond,
- Z: O or NR$^2$,
- A: H; or a lower alkyl which may have from 1 to 4 substituent(s) selected from Group a or Group c; a —CO-lower alkyl which may have from 1 to 4 substituent(s) selected from Group a or Group c; an aryl which may have from 1 to 4 substituent(s) selected from Group a or Group b; a five- to eight-membered monocyclic heteroaryl group which (i) has from 1 to 4 hetero atoms selected from O, S, and N and (ii) may have from 1 to 4 substituent(s) selected from Group a or Group b; a cycloalkyl which may have from 1 to 4 substituent(s) selected from Group a; or a five- to eight-membered saturated heterocyclic group which (i) has at least one N as a ring atom, (ii) may have one O or S as a ring atom, and (iii) may have from 1 to 4 substituent(s) selected from Group a,
- B: an aryl which may have from 1 to 4 substituent(s) selected from Group a or Group b or a five- to eight-membered monocyclic heteroaryl group which (i) has from 1 to 4 hetero atoms selected from O, S, and N and (ii) may have from 1 to 4 substituent(s) selected from Group a or Group b, and
- R$^1$, R$^2$: H; a lower alkyl or —CO-lower alkyl group,
  - Group a: —NH$_2$; —NH$_2$ in a prodrug form; -lower alkylene-NH$_2$; -lower alkylene-NH$_2$ in a prodrug form; —NH-lower alkyl; —N(lower alkyl)$_2$; —NH-lower alkylene-aryl; —NH-aryl; —NH-cycloalkyl; —NH-a five- to eight-membered monocyclic heteroaryl group which has from 1 to 4 hetero atoms selected from O, S, and N; —NHCO-lower alkyl; —NHSO$_2$-lower alkyl; —NHC(NH)NH$_2$; —NHCONH$_2$; —OH; —O-lower alkyl; —CO$_2$H; —CONHOH; —CO$_2$-lower alkyl; —CONH-lower alkyl; or —CON(lower alkyl)$_2$,
  - Group b: -lower alkyl; -halogen atom selected from the group consisting of F, Cl, Br, and I; -lower alkyl having One or more hydrogen atoms substituted by a halogen atom selected from the group consisting of F, Cl, Br, and I; —O-lower alkylene-aryl; —O-aryl; —O-lower alkylene-aryl-O-lower alkyl; —S-lower alkylene-aryl; —S-lower alkylene-aryl-O-lower alkyl; —NO$_2$; or —CN, and
  - Group c: -halogen atom selected from the group consisting of F, Cl, Br, and I; —O-lower alkylene-aryl, —O-aryl; —O-lower alkylene-aryl-O-lower alkyl; —S-lower alkylene-aryl; —S-lower alkylene-aryl-O-lower alkyl; —NO$_2$; —CN; -aryl which may be substituted by a group selected from Group a; -cycloalkyl; -a five- to eight-membered monocyclic heteroaryl group which has from 1 to 4 hetero atoms selected from 0, S, and N; -a five- to eight-membered saturated heterocyclic group having from 1 to 4 hetero atoms selected from O, S, and N; -vinyl; -(1-propenyl); or -ethynyl,
  with the proviso that A is a group other than an ethyl group when X is NH, Y and Z are respectively a bond and B is 2-methylphenyl, and
  wherein —NH$_2$ in the prodrug form means a group selected from the group consisting of (Z)-3-{2-(acetoxy)phenyl}-2-propenoylanino-, (acetoxy) rnethoxycarbonylamino-, 4-azidobenzyloxycarbonylamino-, (5-methyl-2-oxo-1,3-dioxol-4-en-4-yl) methoxycarbonylamino-, and {(2-hydroxyphenyl)(phenyl)methylidene}amino-.

2. The compound or a salt thereof according to claim 1, wherein X is NR$^1$, R$^1$ is H or a lower alkyl, Y is a bond, Z is NH and B is an aryl which may have 1 to 3 substituents selected from —NH$_2$, -lower alkylene-NH$_2$, -lower alkyl, -halogen atom, —CF$_3$ and —O-lower alkyl group.

3. The compound or a salt thereof according to claim 2, wherein A is a lower alkyl group substituted by a group selected from —NH$_2$ and —NH$_2$ in a prodrug form.

4. The compound or a salt thereof according to claim 2, wherein A is a cycloalkyl group substituted by a group selected from —NH$_2$, —NH$_2$ in a prodrug form and -lower alkylene-NH$_2$.

5. A compound selected from 2-(2-aminoethylamino)-4-(3-methylanilino)pyrimidine-5-carboxamide, 2-(2-aminoethylamino)-4-(3-trifluoromethylanilino)pyrimidine-5-carboxamide, 2-(4-aminobutylamino)-4-(3-trifluoromethylanilino)pyrimidine-5-carboxamide, 2-(2-aminoethylamino)-4-(3-bromoanilino)pyrimidine-5-carboxamide, 2-(2-aminoethylamino)-4-(3-nitroanilino) pyrimidine-5-carboxamide, 2-(2-aminoethylamino)-4-(3,5-dimethylanilino)pyrimidine-5-carboxamide, 2-(2-aminoethylamino)-4-(2-naphthylamino)pyrimidine-5-carboxamide, 2-(cis-2-aminocyclohexylamino)-4-(3-methylanilino)pyrimidine-5-carboxamide, 2-(cis-2-aminocyclohexylamino)-4-(3-bromoanilino)pyrimidine-5-carboxamide, 2-(cis- 2-aminocyclohexylamino)-4-(3,5-dichloroanilino)pyrimidine-5-carboxamide and 2- (cis-2-aminocyclohexylamino) -4-(3,4,5-trimethoxyanilino) pyrimidine-5-carboxamide, or a salt thereof.

6. A pharmaceutical composition which comprises the compound of claim 1 or a salt thereof and a pharmaceutically acceptable carrier.

* * * * *

UNITED STATES PATENT AND TRADEMARK OFFICE
CERTIFICATE OF CORRECTION

PATENT NO.    : 6,432,963 B1
DATED         : August 13, 2002
INVENTOR(S)   : Hiroyuki Hisamichi et al.

It is certified that error appears in the above-identified patent and that said Letters Patent is hereby corrected as shown below:

<u>Column 3,</u>
Line 41, delete "a:Th".

<u>Column 6,</u>
Line 27, delete "L:";
Line 58, "s:com-" should read -- com- --.

<u>Column 9,</u>
Lines 40-45, that portion of the formula for compound (Id) reading $H_2\overset{+}{N}\diagup$ should read $H_2N\diagup$ <u>Column 13,</u>
Line 63, delete "E".

<u>Column 15,</u>
Line 4, delete "w".

<u>Column 19,</u>
Line 14, delete "Ad:.";
Line 52, ""170" should read -- 170 --.

<u>Column 20,</u>
Line 12, "4⁻M" should read -- 4 M --;
Line 63, "chloroform:methanel)" should read -- chloroform:methanol) --.

<u>Column 23,</u>
Table 2, column $R^b$ of row Rex 32, "5-$CF_3$" should read -- 3-$CF_3$ --.

UNITED STATES PATENT AND TRADEMARK OFFICE
CERTIFICATE OF CORRECTION

PATENT NO. : 6,432,963 B1
DATED : August 13, 2002
INVENTOR(S) : Hiroyuki Hisamichi et al.

It is certified that error appears in the above-identified patent and that said Letters Patent is hereby corrected as shown below:

Column 31,
Table 5, column A—Z— of row Ex 13, that portion of the formula reading

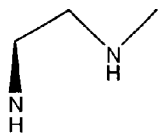   should read   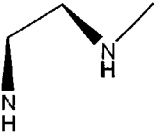

Column 54,
Line 20, "rnethoxycarbonylamino-," should read -- methoxycarbonylamino-, --.

Signed and Sealed this

Sixth Day of May, 2003

JAMES E. ROGAN
*Director of the United States Patent and Trademark Office*